(12) United States Patent
Herrmann et al.

(10) Patent No.: US 8,475,851 B2
(45) Date of Patent: Jul. 2, 2013

(54) PREPARATIONS WITH WOOD EXTRACTS OF LOCUST TREES

(75) Inventors: Martina Herrmann, Hameln (DE); Holger Joppe, Dassel (DE); Imke Meyer, Bodenwerder (DE); Karin Schaper, Wangelnstedt (DE); Thomas Küper, Reken (DE); Julia Betke, Dörentrup (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 13/365,089

(22) Filed: Feb. 2, 2012

(65) Prior Publication Data

US 2012/0195870 A1 Aug. 2, 2012

Related U.S. Application Data

(60) Provisional application No. 61/438,769, filed on Feb. 2, 2011.

(30) Foreign Application Priority Data

Feb. 2, 2011 (EP) .................................... 11153073

(51) Int. Cl.
*A01N 65/00* (2009.01)
(52) U.S. Cl.
USPC ........................................................ 424/725

(58) Field of Classification Search
None
See application file for complete search history.

(56) References Cited

U.S. PATENT DOCUMENTS

| | | |
|---|---|---|
| 2005/0186290 A1 | 8/2005 | Cals-Grierson |
| 2006/0002885 A1 | 1/2006 | Mielke et al. |

FOREIGN PATENT DOCUMENTS

| | | |
|---|---|---|
| DE | 10 2004 032 837 A1 | 2/2006 |
| EP | 1541127 A1 | 6/2005 |
| FR | 2740681 A1 | 5/1997 |
| FR | 2799121 A1 | 4/2001 |

OTHER PUBLICATIONS

Chadenson et al.: "Sur les constiuants flavoniques du levier (*Glediischia triacanihos*)"; Comples Rendus Hebdomadaires des Seances de L'Academie des Sciences, Gauthier-Villars, Paris, FR, Bd. 240, Jan. 1, 1955, pp. 1362-1364.

*Primary Examiner* — Michael Meller
(74) *Attorney, Agent, or Firm* — Novak Druce Connolly Bove + Quigg LLP

(57) ABSTRACT

The present invention relates primarily to the use of locust tree (*Gleditsia*) wood or heartwood extracts as anti-cellulite active substances. The present invention further relates to certain locust-tree wood extracts and mixtures containing locust-tree wood extracts and corresponding cosmetic, dermatological or pharmaceutical preparations, which are suitable in particular for the prevention and treatment of cellulite in humans.

20 Claims, No Drawings

PREPARATIONS WITH WOOD EXTRACTS OF LOCUST TREES

CROSS-REFERENCE TO RELATED APPLICATIONS

This application claims priority under 35 U.S.C. §119(e) to U.S. provisional application No. 61/438,769, filed Feb. 2, 2011, and to European Application No. 11 153 073.9, filed Feb. 2, 2011, the entire contents of which are hereby incorporated by reference.

The present invention relates primarily to the use of locust tree (*Gleditsia*) wood or heartwood extracts as anti-cellulite active substances. The present invention further relates to certain locust-tree wood extracts and mixtures containing locust-tree wood extracts and corresponding cosmetic, dermatological or pharmaceutical preparations, which are suitable in particular for the prevention and treatment of cellulite in humans.

The normal ageing process is generally regarded as the changing of the body in the course of life. Generally a distinction is made between intrinsic (genetically determined) and extrinsic (environmentally conditioned) ageing. The exogenous factors that lead to premature skin ageing (so-called photo-ageing) include mainly UV exposure, social drugs (tobacco, alcohol) and climate or weather effects. With increasing age, adults suffer a continuous loss of organ-specific functions, which is associated with various changes, for example a decrease in metabolic activity, a low cell division rate, a reduced capacity for DNA repair, stiffening of vessel walls and impaired peripheral blood circulation. All these aspects are closely interrelated.

In the context of ageing, there are also pronounced structural changes of the skin. They occur at cellular and non-cellular level, affect all layers of the skin and are visible both micro- and macromorphologically. The epidermis (the outer skin layer) becomes thinner owing to a decrease in the mitotic rate of the basal cells. In addition, increased water loss through diffusion, decreased elasticity, a coarser outer structure and wrinkle formation may be observed. The aged dermis is characterized by few fibroblasts with lower activity. Additionally, reduced production of tropocollagen, hyaluronic acid and elastin may be observed, as well as reduced secretion from sebaceous glands and sweat glands. The subcutis (subcutaneous fatty tissue) suffers a loss of volume.

Calorie restriction, i.e. a food intake reduced by 20 through 50%, leads in various organisms, including mammals, to delayed ageing and has health-promoting effects. Thus, the occurrence of age-related diseases such as diabetes and cardiovascular diseases is reduced or deferred and improved protection against for example heat and oxidative stress is induced.

Cellulite—also known by the synonyms protrusio cutis and colloquially as orange-peel skin—is a cosmetic-aesthetic problem, which is associated with formation of dimples and depressions in the skin and nodulation of the subcutaneous fatty tissue. Cellulite can occur anywhere on the human body, but the outer surface and back of the thighs and the buttocks are the most commonly affected. The breasts, lower abdomen, upper arms or neck are also sometimes affected by cellulite.

Cellulite may certainly occur regularly on parts of the human body with excessive fat deposition, but being overweight is not a precondition for its occurrence. Even slim women increasingly have pronounced cellulite effects. There is, however, certainly a correlation between the severity of cellulite and the percentage of fat in the tissue.

The sex-specific anatomical structure of human skin has a considerable influence on the development of cellulite. Thus, cellulite is observed only rarely in men, whereas it affects 80%-90% of all women. In particular, the structure of the dermis has an effect on the relief of the skin. Thus, in men, when the skin is squeezed, the fat chambers are retained by intersecting connective tissue septa and the associated clamp-like inclusion of the fat cells. In contrast, in women, the fat chambers, which are separated from one another in tubular fashion, and enclosed by radial connective tissue septa, bulge up when squeezed.

The conventional methods of treatment of cellulite try to promote blood supply to the affected areas of the skin and exert a beneficial influence on the connective tissue structure, for example through massage, lymph drainage, diet, sport, magnetic fields or also liposuction.

Cellulite can also be accompanied by abnormal sensory perception, such as skin irritation and skin inflammation, of the affected regions of the body.

Skin inflammation means, in connection with this application, any change of the skin that causes abnormal sensory perception in humans and/or is manifested by dry, reddened and/or inflamed skin. The term "abnormal sensory perception" of course also includes conditions such as pruritus or pain. Skin irritation can in particular comprise phenomenologically varied skin conditions: sensible skin, sensitive skin (including sensitive scalp), vulnerable skin, atopic skin, irritated skin, inflamed skin, each being manifested, when of increased severity, as reddening of the skin, so-called erythema.

The problem of "sensible skin" affects a growing number of adults and children. It is now assumed that up to 50% of the population have sensible skin. Sensible skin denotes skin with a lowered stimulus threshold for irritants, such as hyper-reactive and intolerant, but also atopic skin. In people with sensible, sensitive or vulnerable skin, a phenomenon called "stinging" (English "to sting"=injure, burn, cause pain) can be observed. Typically, disturbing phenomena united by the terms "stinging" or "sensitive skin" are reddening of the skin, formication, tingling, tautness and burning of the skin, and pruritus. They can be caused by stimulating environmental conditions, e.g. massage, action of detergents, weather effects such as heat, cold, dryness, but also damp heat, thermal radiation and UV radiation, e.g. sunlight, or psychological stress.

"Sensitive" scalp is also characterized by reddening of the skin, formication, tingling, burning and pruritus. It is caused for example by soap, shampoos or other hair care products, surfactants, hard water with high lime concentrations and/or mechanical stress. Erythema and hyperseborrhoea (excessive sebaceous secretion) of the scalp, and dandruff, are often associated with the phenomena described.

At a level of approx. 10-20% of the population of industrialized countries, there is an increasing trend towards atopy, a familial hypersensitivity of the skin and mucosae to substances in the environment, with an increased tendency to develop hypersensitivity reactions of the immediate type (allergies) to substances from the natural environment. Atopy is presumably genetically determined. Atopy can be manifested as atopic dermatitis. In this, the skin barrier is damaged, the skin is often inflamed and itches. Sirtuins (sirtuin proteins) are a class of $NAD^+$-dependent histone and protein deacetylases, which are upregulated under calorie restriction. For mammals, i.e. also for humans, so far 7 sirtuins (SIRT1-7) have been described, and of these, SIRT1 has received most study. The localization in the cells is very varied for the 7 human sirtuins, thus apparently SIRT6 and SIRT7 are localized in the cell nucleus, SIRT1 mainly in the cell nucleus but also in the cytoplasm, SIRT2 generally in the cytoplasm but also in the cell nucleus and SIRT3, SIRT4 and SIRT5 exclusively in the mitochondria. Sirtuins deacetylate, as histone deacetylases (HDAC) of class III, the histone proteins by a $NAD^+$-dependent mechanism. These and other posttranslational changes on the side chains of individual amino acids of histone proteins contribute to regulation of the activation and turning-off of particular gene segments. These control mechanisms of gene expression beyond the DNA sequence, which is not altered, are designated as epigenetics.

Furthermore, sirtuins also deacetylate a number of important non-histone proteins, including, among others, important transcription factors, for example p53, PGC-1alpha, NF-κB, p300 and transcription factors from the FOXO group and thus regulate their activity. These protein substrates are among the central regulators of cellular metabolism and energy metabolism, and play an important role in e.g. inflammations and the cellular stress response.

The anti-inflammatory effect of SIRT is based among other things on suppression of NF-κB activity and/or on cyclooxygenase-2 (COX-2) inhibition. Excessive activation of NF-κB has been described for old-age skin and thus links inflammation to ageing. One effect of NF-κB activation is expression of matrix metalloproteinases (MMPs), enzymes which degrade various fibrous proteins of the extracellular matrix such as collagen and elastin.

The erythematous action of the ultraviolet component of solar radiation or artificial radiation on the skin is generally known. Whereas rays with a wavelength of less than 290 nm (the so-called UVC region) are absorbed by the ozone layer in the Earth's atmosphere, rays in the region between 290 nm and 320 nm, the so-called UVB region, cause erythema, a simple sunburn or even more or less severe burns.

Erythematous skin symptoms also occur as concomitant effects in certain skin diseases or disorders. For example, the typical rash as a symptom of acne is regularly reddened to a varying degree and impairs the wellbeing of the person affected even in mild cases. Cosmetic activators of SIRT can therefore be used on the one hand as active substances against ageing, in particular as active substances against skin ageing (in the context of this text, also designated as "anti-ageing active substances"), and as general cellular stress protectors. Furthermore, they offer advantages as anti-inflammatory active substances and prevent ageing caused by inflammation (inflammageing) by reducing proinflammatory cytokines, which leads to a uniform skin tone and reduces moles.

The regulation of fat metabolism in human fatty tissue for reducing the stored amount of lipids can in principle take place by three routes:

Route (i)—Adipogenesis: the differentiation of the precursor cells of fat cells, called preadipocytes, to actual fat cells (known as adipocytes), which can store triglycerides, can be inhibited. Put simply, inhibition of route (i) prevents the buildup of cellulite, as the number of fat cells does not increase.

Route (ii)—Lipogenesis: The storage of triglycerides in the adipocytes can be prevented or inhibited. Put simply, inhibition of route (ii) prevents the storage of further triglycerides (fats) in the cell, existing fat cells do not store any new fat. Through the natural fat metabolism, on inhibition of route (ii) the fat content in the cell decreases.

Route (iii)—Lipolysis: Increased/intensified hydrolysis of lipids already stored in the adipocytes is possible by targeted stimulation. This results in reduction of the amount of lipids already contained in subcutaneous fatty tissue. Put simply, stimulation of route (iii) intensifies the degradation of the fats already present in the cell, and in contrast an inhibiting, i.e. antagonistic, action with respect to route (iii) inhibits or prevents fat degradation.

The differentiation of cells is the alteration of the regulation of the genetic activity of a cell, so that via transcription and protein biosynthesis, various protein populations are produced in the cells and the cells are differentiated in appearance and function. Thus, it is only after differentiation that adipocytes express enzymes that are necessary for the storage of fats. These enzymes are only expressed to a very slight extent, or not at all, in their precursor cells, undifferentiated preadipocytes.

Cosmetic preparations that are intended for the prevention and treatment of cellulite have already been proposed in the literature.

EP 1 234 572 describes a cosmetic preparation from at least one isoflavone-aglycon from the group genistein, daidzein, glycitein, formononetin, tectorigenin, irigenin, biochanin A, O-desmethylangolensin, equol, orobol, santal, pratensin and apiosylpuerarin, in particular genistein and/or daidzein, for the treatment of cellulite.

DE 10 2004 032 837 describes a cosmetic preparation from certain bioquinones and isoflavonoids, preferably genistein, for the prevention of cellulite. It is stated that the action of this preparation is due to improvement of cell metabolism. It is not evident which mechanism of cell metabolism is improved.

WO 2010/048114 describes natural substances for modifying adipocyte physiology.

Journal of Biochemistry 2004, 135(1), 85-91 describes the inhibitory effect of fisetin on fatty acid synthase.

According to Biochem. Pharmacol. 1992, 44, 1307-1315, lipolysis is basically not stimulated by phosphodiesterase inhibitors, as lipolysis is subject to the influence of various factors.

WO 2005/002672 discloses a number of compounds that stimulate sirtuin enzyme activity, including naturally occurring substances including resveratrol, by far the most mentioned stimulator of SIRT1 enzyme activity, flavonoids such as fisetin, luteolin, 3,6,3',4'-tetrahydroxyflavone, quercetin, naringin and 3,5,7,3',4'-pentahydroxyflavanone. However, it seems uncertain to what extent the in-vitro test used in WO 2005/002672 for determining the stimulation of the SIRT1 enzyme activity using a synthetic, artificial acylated peptide substrate reflects the true situation at all, as no stimulating effect by resveratrol could be found on actual biological substrates (Chem. Biol. Drug Des. 2009, 74, 619-624). Also it cannot be concluded, from a stimulating action on sirtuin enzyme activity, that there is simultaneous stimulation of sirtuin protein expression.

The primary object to be achieved by the present invention was to provide agents with anti-cellulite efficacy. The agents to be provided should be usable in numerous different preparations, in particular in cosmetic, dermatological and pharmaceutical preparations. Preferably the agents should be of natural origin, easily producible and with good storage properties. Furthermore, methods of production for corresponding agents and uses thereof should be provided.

It would be advantageous if the agent being sought in addition were to have a beneficial effect on skin irritation, which is often associated with cellulite.

Surprisingly, it was found in our own extensive research that *Gleditsia* wood extracts are very suitable as anti-cellulite active substances.

In a first aspect the present invention relates to the use of a wood extract of a plant of the genus *Gleditsia* i) for producing a cosmetic or pharmaceutical preparation for the, preferably topical, prevention, treatment or reduction of cellulite,
and/or
(ii) for the non-therapeutic
inhibition of the differentiation of preadipocytes,
and/or
inhibition of lipogenesis in adipocytes,
and/or
reduction of the amount of lipids contained in subcutaneous fatty tissue.

The *Gleditsia* wood extracts according to the invention or to be used according to the invention additionally show SIRT-stimulating, i.e. SIRT-activating, efficacy, in particular with respect to SIRT1.

In particular, the increase in the SIRT1 protein level, i.e. the SIRT1 protein content, or the enzyme activity in the white adipose tissue presumably leads to further reduced adipogenesis and reduced lipid storage. Also on the basis of these properties, the *Gleditsia* wood extracts according to the invention or to be used according to the invention act as active substances for the prevention and reduction of cellulite.

The *Gleditsia* wood extracts according to the invention or to be used according to the invention are in addition anti-irritant active substances.

On the whole, the *Gleditsia* wood extracts according to the invention or to be used according to the invention show, along with the required anti-cellulite efficacy, additionally SIRT-stimulating/activating and anti-irritant efficacy. The *Gleditsia* wood extracts according to the invention or to be used according to the invention can therefore be used as anti-ageing active substances, in particular as active substances against skin ageing.

The use of an extract of the wood, preferably of the heartwood, of *Gleditsia triacanthos* is preferred according to the invention, as particularly good results were achieved with these.

The locust trees (*Gleditsia*), also called honey locusts, are a plant genus from the legume family (Fabaceae). They are indigenous to the temperate and subtropical regions of North and South America and to parts of temperate and subtropical Asia and tropical Africa.

*Gleditsia triacanthos*, also known as American locust tree or (false) Christ's thorn, is a deciduous tree, up to 20 m tall, indigenous to the central and eastern parts of the USA. The trunk is "armed" with large clusters of strong, branched thorns, which are up to 30 cm long, which led to the name (false) Christ's thorn. The legumes are striking; in autumn and winter they hang from the trees as pods about 25 (in hot situations even up to 50) centimeters long and 2.5 through 4 centimeters wide. They are twisted in a spiral and they turn brown later. In Central Europe, *Gleditsia triacanthos* is completely winter-hardy and is often planted there in parks and public gardens.

The seeds of the honey locust are edible raw or cooked and contain large amounts of polysaccharides. For these, FR 2067649 describes the cosmetic use as hair softening and defrizzing active substance and GB 1,065,910 describes the use as excipient for medicinal products.

The fruit (CN 101317960) or an ethanolic fruit extract (Int. J. Mol. Med. 2009, 23(1):121-9) and the thorns (CN 101224287) of the Chinese locust tree (*G. sinensis*) are described, sometimes in combination with other plant (parts) in traditional Chinese medicine, as anti-rheumatic, anti-arthritic, anti-inflammatory and cyclooxygenase-2 inhibitor.

The Japanese locust tree (*G. japonica*) is described as part of compositions with hair growth promoting, dandruff and pruritus inhibiting efficacy (JP 2001288047 and JP 2000044439) and with activity preventing hair graying (JP 2001131026).

In Yakugaku Zasshi 1957, 77, 1208-1210, wood raspings from the heartwood of *G. japonica* were extracted with methanol or ethyl acetate and analyzed. In the extracts, fisetin, fustin and gledistin were identified as components of the heartwood of *G. japonica*.

Compt. Rend. Acad. Sci., Paris, 1955, 240, 1362-1364 describes the exhaustive extraction of *Gleditsia triacanthos* wood powder with ether in the cold and the subsequent isolation of fustin and fisetin.

The composition of a plant part of one species of a genus is not necessarily applicable to the composition of another species of the same genus.

Furthermore, the components and therefore the biological activity of extracts are as a rule highly dependent on the plant part extracted in each case. This is demonstrated for example in Yakugaku Zasshi 1957, 77 for the substance class of the saponins, a principal constituent of the fruits of *Gleditsia japonica*. These saponins were only found in the mesocarp of the fruits, but not in other parts of the fruit or other parts of the plant such as bark or thorns. Moreover, the extraction conditions, in particular the extractant used, also play a role.

The wood or heartwood of *Gleditsia triacanthos* is very durable, colored yellowish green to reddish brown, and hard. It is used locally for the production of pallets and crates and generally for furniture-making and interior finishing. No information is available on topical or oral use, in particular topical or oral cosmetic, dermatological or pharmaceutical use of wood or heartwood extracts of *Gleditsia triacanthos*.

Heartwood designates the physiologically no longer active, generally darker, inner zone in the trunk cross-section, which is clearly different from the outer, light-colored sapwood.

An extract from wood, preferably from heartwood, of plants of the genus *Gleditsia*, here preferably of the species *Gleditsia triacanthos*, is used according to the invention.

In the context of the present text, an extract from wood, preferably heartwood, of plants of the genus *Gleditsia*, is designated as dry extract, preferably produced or producible by the method according to the invention described below, after complete removal of the water and of the extractant or extractants (for the case when a plurality of extractants are used).

A method that is suitable according to the invention for preparing an extract from *Gleditsia* wood or heartwood comprises the following steps:
(1) providing wood, preferably wood raspings, from plants of the genus *Gleditsia*, preferably of the species *Gleditsia triacanthos*,
(2) adding, to the wood provided in step (1), an extractant selected from the group consisting of water, methanol, ethanol, n-propanol, isopropanol, acetone, ethyl acetate, supercritical carbon dioxide and mixtures of two or a plurality of these extractants,
(3) for up to 24 h, extracting the wood, to which the extractant was added in step (2), to obtain a wood extract, and
(4) optionally partially or completely removing the extractant or extractants used in step (2).

The invention further relates to novel extracts produced or producible with a method comprising or consisting of the steps:
(1) providing wood, preferably wood raspings, preferably heartwood raspings, from plants of the genus *Gleditsia*, preferably of the species *Gleditsia triacanthos*, (2) adding, to the wood provided in step (1), an extractant selected from the group consisting of water, methanol, ethanol, n-propanol, isopropanol, acetone, ethyl acetate, supercritical carbon dioxide and mixtures of two or a plurality of these extractants, (3) for up to 24 h, extracting the wood, to which the extractant was added in step (2), to obtain a wood extract, and (4) optionally partially or completely removing the extractant or extractants used in step (2), with the proviso that the extracts obtained by extraction of the heartwood of *Gleditsia japonica* with methanol or with ethyl acetate are excluded.

The following are preferably selected as wood raspings: wood shavings, wood chips, for example planing chips, and/or wood flour, for example sawdust, and/or wood rasped or comminuted in some other way.

For producing a *Gleditsia* wood extract according to the invention or to be used according to the invention, the ratio of the weight of extractant to the weight of wood is preferably adjusted so that it is at least twice the weight of extractant and preferably not more than 30 times the weight of extractant, in each case relative to the weight of wood used. The weight ratio of extractant to wood is preferably in the range from 3:1 through 25:1, particularly preferably in the range from 4:1 through 20:1, even more preferably in the range from 5:1 through 15:1.

The extraction time for the execution of step (3) is, according to the invention, preferably at most 24 hours. It is preferable to extract the wood raspings in step b) for at least 1 h, in particular at least 2 h. The extraction time required for producing an extract for use in cosmetic, dermatological or pharmaceutical preparations is preferably at most 16 h, preferably at most 8 h and particularly preferably at most 4 h. The extraction time is selected depending on the quality of the wood to be extracted and on the other extraction conditions, in particular the extraction temperature.

Additionally, it is particularly preferable to carry out the extraction in step (3) with heating and/or reflux of the extractant. The extraction temperature is set depending on the extractant used.

Extraction as a rule preferably takes place at ambient pressure, but can of course also be carried out at reduced pressure or overpressure. Extraction preferably takes place at a pressure in the range from 800 through 1200 mbar, preferably at a pressure in the range from 900 through 1100 mbar.

Extraction is preferably carried out at a temperature in the range from 40 through 120° C., preferably in the range from 50 through 100° C.

When using a water-containing or ethanol-containing extractant, in particular a mixture of extractants comprising or consisting of water and ethanol, an extraction temperature of 50-100° C. is preferred, preferably at a pressure in the range from 800 through 1200 mbar, preferably at a pressure in the range from 900 through 1100 mbar, even more preferably at a pressure in the range from 950 through 1050 mbar.

The wood extract according to the invention or to be used according to the invention should, for use in cosmetic, dermatological or pharmaceutical preparations, be largely free or completely free from organic extractants used in step (2). The organic extractant or organic extractants and optionally water can be removed as completely as possible in step (4) by a suitable method (e.g. distillation, drying, lyophilization and similar methods).

Therefore a method of preparing a wood extract according to the invention or to be used according to the invention comprises the step (4) partially or completely removing the organic extractant or organic extractants used in step (2), preferably completely removing the organic extractant or organic extractants used in step (2), preferably completely removing the organic extractant or organic extractants and water used in step (2).

The extractant(s) in step (2) are preferably selected from the group consisting of water, methanol, ethanol, n-propanol, isopropanol and mixtures of two or a plurality of these extractants, as a higher activity in the sense of the present invention was found for the *Gleditsia* wood extracts obtainable with these extractants.

Preferred extracts according to the invention are produced or are producible with a method comprising or consisting of the steps:

(1) providing wood raspings, preferably heartwood raspings, of the species *Gleditsia triacanthos*, (2) adding, to the wood provided in step (1), an extractant selected from the group consisting of water, methanol, ethanol, n-propanol, isopropanol and mixtures of two or a plurality of these extractants, (3) for 1 up to 16 h, extracting the wood, to which the extractant was added in step (2), to obtain a wood extract, and (4) optionally partially or completely removing the extractant or extractants used in step (2).

Further preferred extracts according to the invention are produced or producible with a method comprising or consisting of the steps:

(1) providing heartwood raspings of the species *Gleditsia triacanthos*, (2) adding, to the wood provided in step (1), an extractant selected from the group consisting of water, ethanol and mixtures of water and ethanol, (3) for 1 up to 8 h, extracting the wood, to which the extractant was added in step (2), to obtain a wood extract, and (4) preferably partially or completely removing the organic extractant or organic extractants used in step (2).

Further preferred extracts according to the invention are produced or producible with a method comprising or consisting of the steps:

(1) providing heartwood raspings of the species *Gleditsia triacanthos*, (2) adding, to the wood provided in step (1), an extractant that comprises or consists of at least 80 wt. %, preferably at least 90 wt. %, preferably at least 95 wt. % water and ethanol, (3) for 1 up to 8 h, preferably 1 through 4 h, extracting the wood, to which the extractant was added in step (2), to obtain a wood extract, and (4) partially or completely removing the organic extractant or organic extractants used in step (2).

When an extractant comprises water and ethanol or consists of water and ethanol, the weight ratio of water to ethanol in step (2) is preferably in the range from 3:1 through 1:3, preferably in the range from 2:1 through 1:2, particularly preferably in the range from 3:2 through 2:3, even more preferably in the range from 5:4 through 4:5, most preferably at 1:1.

The extracts according to the invention are not extracts such as are obtained by extraction of the heartwood of *Gleditsia triacanthos* with diethyl ether.

Preferably the extracts according to the invention are not extracts such as are obtained by extraction of the heartwood of *Gleditsia triacanthos* with ether.

The *Gleditsia* wood extract according to the invention or to be used according to the invention described above can preferably be further processed to a *Gleditsia* wood extract according to the invention in solid form, by supplementing the method of production according to the invention with the steps:

(5) adding a pharmaceutically and/or cosmetically acceptable solid carrier to the liquid extract concentrated by a suitable method (e.g. distillation), and
(6) drying the extract, with the carrier added, by a suitable method (e.g. spray-drying or conveyor drying)

According to the invention, step (5) can also be omitted, and in this case a powder of higher concentration is obtained than when a pharmaceutically and/or cosmetically acceptable carrier is added. Said solid that is at least non-toxic to the organism on which it is to be used is pharmaceutically or cosmetically acceptable. A preferred cosmetically acceptable solid is powdered maltodextrin.

Extracts according to the invention with good storage properties can be produced in this way. By adjusting the mixture ratio of the extract obtained and of the pharmaceutically and/or cosmetically acceptable carrier, the final concentration of the active substances contained in the powdered extract can be adjusted advantageously easily.

Furthermore, the *Gleditsia* wood extract according to the invention or to be used according to the invention or a *Gleditsia* wood extract-containing solid or liquid preparation can also be further processed according to the invention by encapsulation. In this, the extract or the solid or liquid preparation is encapsulated with a solid shell material, which is preferably selected from starches, degraded or chemically or physically modified starches (in particular dextrins and maltodextrins), gelatins, gum arabic, agar-agar, ghatti gum, gellan gum, modified and unmodified celluloses, pullulan, curdlan, carrageenans, alginic acid, alginates, pectin, inulin, xanthan gum and mixtures of two or a plurality of the stated substances.

Furthermore, the *Gleditsia* wood extract according to the invention or to be used according to the invention can also be further processed to a liquid mixture or preparation according to the invention, by mixing the *Gleditsia* wood extract according to the invention or to be used according to the invention with a liquid diluent, preferably selected from the group consisting of 1,2-propanediol, 1,3-propanediol, 1,2-butanediol, 1,3-butanediol, 1,4-butanediol, glycerol, 1,2-pentanediol, neutral oils, mineral oils, silicone oil, vegetable oils, fatty alcohols, fatty acid esters, ethanol, water and mixtures of two or a plurality of the stated diluents.

These diluted liquid *Gleditsia* wood extracts according to the invention or to be used according to the invention are in particular very suitable for further processing for cosmetic, dermatological and pharmaceutical purposes. Optionally these mixtures or preparations according to the invention are produced with addition of a preservative, a solubilizer, an antioxidant and/or stabilizer.

The invention further relates to a mixture containing
(a) a wood extract of a plant of the genus *Gleditsia*, preferably a wood extract characterized above as preferable,
and
(b) one or a plurality of polyhydric alcohols with 3 or 4 carbon atoms, preferably selected from the group consisting of 1,2-propanediol, 1,3-propanediol, 1,2-butanediol, 1,3-butanediol, 1,4-butanediol and glycerol,
and optionally additionally
(c) water
and/or
(d) ethanol.

Such mixtures are particularly suitable for incorporating in cosmetic, dermatological or pharmaceutical preparations, in particular in preparations in the form of emulsions.

Preferably the total amount of constituent (b) of a mixture according to the invention is at least 10 wt. %, preferably 20 through 80 wt. %, even more preferably 35 through 70 wt. %, in each case relative to the total weight of the mixture.

Preferably the total amount of water in a mixture according to the invention is at least 5 wt. %, preferably 10 through 70 wt. %, even more preferably 15 through 60 wt. %, in each case relative to the total weight of the mixture.

Preferred mixtures according to the invention comprise
(a) a heartwood extract of a plant of the genus *Gleditsia*, preferably a heartwood extract of *Gleditsia triacanthos*,
(b) one or a plurality of polyhydric alcohols with 3 or 4 carbon atoms, preferably selected from the group consisting of 1,2-propanediol, 1,3-butanediol and glycerol,
and
(c) water.

A *Gleditsia* wood extract according to the invention or to be used according to the invention can, in numerous cases, also be used advantageously in combination with one or a plurality of preservatives. Preservatives are preferably selected such as benzoic acid, its esters and salts, propionic acid and its salts, salicylic acid and its salts, 2,4-hexadienoic acid (sorbic acid) and its salts, esters of p-hydroxybenzoic acid (parabens), formaldehyde and paraformaldehyde, 2-hydroxybiphenyl ether and its salts, 2-zinc sulphidopyridine-N-oxide, inorganic sulphites and bisulphites, sodium iodate, chlorobutanol, 4-ethyl mercury(II)-5-amino-1,3-bis(2-hydroxybenzoic acid, its salts and esters, dehydroacetic acid, formic acid, 1,6-bis(4-amidino-2-bromophenoxy)-n-hexane and its salts, the sodium salt of ethyl mercury(II)-thiosalicylic acid, phenyl mercury and its salts, 10-undecylenic acid and its salts, 5-amino-1,3-bis(2-ethylhexyl)-5-methyl-hexahydro-pyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)-urea, 4-chloro-m-cresol, 2,4,4'-trichloro-2'-hydroxy-diphenyl ether, 4-chloro-3,5-dimethylphenol, 1,1'-methylene-bis(3-(1-hydroxymethyl-2,4-dioximidazolidin-5-yl)urea), poly-(hexamethylene diguanide)-hydrochloride, 2-phenoxyethanol, hexamethylenetetramine, 1-(3-chloroallyl)-3,5,7-triaza-1-azonia-adamantane chloride, 1-(4-chlorophenoxy)1(1H-imidazol-1-yl)-3,3-dimethyl-2-butanone, 1,3-bis(hydroxymethyl)-5,5-dimethyl-2,4-imidazolidindione, benzyl alcohol, octopirox, 1,2-dibromo-2,4-dicyanobutane, 2,2'-methylene-bis(6-bromo-4-chlorophenol), bromchlorophene, mixture of 5-chloro-2-methyl-3(2H)-isothiazolinone and 2-methyl-3 (2H)isothiazlinone with magnesium chloride and magnesium nitrate, 2-benzyl-4-chlorophenol, 2-chloroacetamide, chlorhexidine, chlorhexidine acetate, chlorhexidine gluconate, chlorhexidine hydrochloride, 1-phenoxypropan-2-ol, N-alkyl($C_{12}$-$C_{22}$)trimethyl-ammonium bromide and chloride, 4,4-dimethyl-1,3-oxazolidine, N-hydroxymethyl-N-(1, 3-di(hydroxymethyl)-2,5-dioxoimidazolidin-4-yl)-N'-hydroxy-methylurea, 1,6-bis(4-amidino-phenoxy)-n-hexane and its salts, glutaraldehyde, 5-ethyl-1-aza-3,7-dioxabicyclo (3.3.0)octane, 3-(4-chlorophenoxy)-1,2-propanediol, hyamines, alkyl-($C_8$-$C_{18}$)-dimethyl-benzylammonium chloride, alkyl-($C_8$-$C_{18}$)-dimethyl-benzylammonium bromide, alkyl-($C_8$-$C_{18}$)-dimethyl-benzylammonium saccharinate, benzylhemiformal, 3-iodo-2-propinyl-butylcarbamate, sodium hydroxymethyl-aminoacetate or sodium hydroxymethyl aminoacetate.

The total amount of preservatives (one or a plurality of substances) is preferably in the range from 0.05 through 5 wt. %, preferably in the range from 0.1 through 2 wt. %, even more preferably in the range from 0.2 through 1.5 wt. %, particularly preferably in the range from 0.3 through 1 wt. %, in each case relative to the total weight of the mixture.

Preferred preservatives are selected from the group consisting of benzoic acid, its esters and salts, propionic acid and its salts, 2,4-hexadienoic acid (sorbic acid) and its salts, esters of p-hydroxybenzoic acid (parabens), benzyl alcohol, 1-phenoxypropan-2-ol and 2-phenoxyethanol.

Further preferred mixtures according to the invention comprise
(a) a heartwood extract of a plant of the genus *Gleditsia*, preferably a heartwood extract of *Gleditsia triacanthos*,
(b) 1,2-propanediol, 1,3-butanediol and/or glycerol, preferably in a total amount of 20 through 80 wt. %, preferably 40 through 70 wt. %, in each case relative to the total weight of the mixture,
(c) water
and
one or a plurality of preservatives, preferably selected from the group consisting of benzoic acid and its salts, 2,4-hexadienoic acid (sorbic acid) and its salts, esters of p-hydroxybenzoic acid (parabens) and 2-phenoxyethanol, wherein the total amount of preservatives is preferably in the range from 0.2 through 1.5 wt. %, more preferably in the range from 0.3 through 1 wt. %, in each case relative to the total weight of the mixture.

As a result, the mixtures according to the invention acquire particularly high storage stability.

In a preferred embodiment a mixture according to the invention contains at least one preservative, preferably at least two preservatives from the group benzoic acid, sodium benzoate, potassium benzoate, sorbic acid, sodium sorbate and potassium sorbate.

In a preferred embodiment the pH of a mixture according to the invention is preferably in the range from 3 through 7, preferably in the range from 4 through 6, in each case at 25° C. The pH of a mixture according to the invention is preferably adjusted by adding citric acid and/or lactic acid.

Preparations according to the invention containing a *Gleditsia* wood extract according to the invention or to be used according to the invention or a mixture according to the invention influence cellulite with respect to the amount of stored lipid, with the lipid content in human subcutaneous fatty tissue being reduced.

Thus, cellulite is prevented, treated or reduced by a preparation containing a *Gleditsia* wood extract according to the invention or to be used according to the invention in particular through the positive influence on routes (i) (adipogenesis) and (ii) (lipogenesis) described above.

The *Gleditsia* wood extracts according to the invention or to be used according to the invention show a pronounced action in the treatment of cellulite, for example detectable by means of echographic determination of the subcutis layer thickness, in particular for preventing increased formation of fat depots in the skin and/or cellulite, by reducing the lipid content in human subcutaneous fatty tissue.

The invention therefore also relates to preparations, preferably cosmetic preparations, containing a corresponding effective amount of a *Gleditsia* wood extract according to the invention or to be used according to the invention, in particular for the topical treatment and prevention of increased formation of fat depots in the skin and/or cellulite.

Moreover, the preparations according to the invention have a beneficial effect on skin irritations, which may accompany cellulite, since—as already explained above—the *Gleditsia* wood extracts according to the invention or to be used according to the invention have, in addition to anti-cellulite efficacy, additionally SIRT-stimulating/activating and anti-irritant efficacy.

The present invention further relates to a cosmetic, dermatological or pharmaceutical preparation, containing a wood extract of a plant of the genus *Gleditsia*,
(i) for use in a method of prevention, treatment or reduction of cellulite,
and/or
(ii) in a sufficient amount for
inhibition of the differentiation of preadipocytes,
and/or
inhibition of lipogenesis in adipocytes,
and/or
reduction of the amount of lipids contained in subcutaneous fatty tissue.

A preferred preparation according to the invention contains a wood extract according to the invention, preferably in one of the embodiments characterized above as preferable, or a mixture according to the invention, preferably in one of the embodiments characterized above as preferable.

A further preferred preparation according to the invention contains a wood extract according to the invention, preferably a heartwood extract, of *Gleditsia triacanthos*, preferably in one of the embodiments characterized above as preferable.

It was found, moreover, that a wood extract according to the invention or to be used according to the invention displays a higher activity in the sense of the present invention, if the *Gleditsia* wood extract contains fustin (3,3',4',7-tetrahydroxyflavanone) and preferably contains both fustin and fisetin (3,3',4',7-tetrahydroxyflavone).

Furthermore, it was found in our own further research that neither fustin nor fisetin in corresponding concentration showed an activity with respect to adipogenesis (see example 2). Therefore these two compounds are not, or at least not notably, responsible for the adipogenesis inhibiting action of a wood extract according to the invention or to be used according to the invention.

Therefore the efficacy of the wood extracts according to the invention or to be used according to the invention is based on substances that have not yet been identified or characterized. In the extraction conditions stated above, in which fustin, preferably fustin and fisetin, are extracted from the *Gleditsia* wood, the active substances that have not yet been identified or characterized, which are responsible for the efficacy in the sense of the present invention, are extracted.

A preferred *Gleditsia* wood extract according to the invention or to be used according to the invention therefore contains fustin, preferably fustin and fisetin.

Correspondingly, a preferred mixture according to the invention or a preferred preparation according to the invention contains a wood extract according to the invention or to be used according to the invention, which contains fustin and preferably additionally fisetin.

A preferred *Gleditsia* wood extract according to the invention or to be used according to the invention contains, in addition to fustin, also protocatechuic acid (3,4-dihydroxybenzoic acid), preferably fustin, fisetin and protocatechuic acid.

In a preferred embodiment, a wood extract according to the invention or to be used according to the invention, a mixture according to the invention or a preparation according to the invention is free from gleditsin.

Important fields of application are cosmetic, in particular dermatological preparations, which (apart from the extract according to the invention) are composed as usual and serve for cosmetic, in particular dermatological, light protection, for the treatment, care and cleaning of the skin and/or of the hair or as make-up product in decorative cosmetics. Correspondingly, said preparations can, depending on their structure, be used for example as skin protective cream, day cream or night cream, eye cream, sunscreen or after-sun lotion, nutrient cream, care mask, gel-pads, face lotion, moist care and cleaning wipes, cleansing milk, cleansing soap, foam or shower gel, deodorant, antiperspirant, hair shampoo, hair care products, hair conditioner, hair coloring, hair styling products and can preferably be in the form of emulsion, lotion, milk, fluid, cream, aqueous-dispersion gel, balm, spray, alcoholic or aqueous/alcoholic solution, foam, powder, liquid soap, soap bar, shampoo, roll-on, stick or make-up. In hair treatment products, use is preferably directed at the scalp.

Another aspect of the present invention relates to oral care products (oral hygiene products), wherein the oral hygiene products are preferably in the form of toothpaste, tooth cream, tooth gel, tooth powder, tooth cleaning liquid, tooth cleaning foam, mouthwash (ready for use or as concentrate), tooth cream and mouthwash as 2-in-1 product, sugar-free sweets, mouth spray, dental floss or dental-hygiene chewing gum.

The amount of a *Gleditsia* wood extract according to the invention or to be used according to the invention, preferably a *Gleditsia triacanthos* wood extract, in a cosmetic, dermatological or pharmaceutical preparation according to the invention is, relative to the weight of the dry extract (as defined above), preferably in the range from 0.00001 through 10 wt. %, preferably in the range from 0.0001 through 5 wt. %, even more preferably in the range from 0.001 through 2 wt. %, particularly preferably in the range from 0.001 through 1 wt. %, quite particularly preferably in the range from 0.002 through 0.5 wt. % and most preferably in the range from 0.002 through 0.2 wt. %, in each case relative to the total weight of the cosmetic, dermatological or pharmaceutical preparation.

The *Gleditsia* wood extracts according to the invention or to be used according to the invention or solid or liquid formulations or mixtures containing a *Gleditsia* wood extract according to the invention can be incorporated without any difficulty in common cosmetic or dermatological formulations such as pump sprays, aerosol sprays, creams, ointments, tinctures, lotions, nail care products and the like. These cosmetic and/or dermatological formulations containing *Gleditsia* wood extract can otherwise be composed as usual and serve for the treatment of the skin and/or of the hair in the sense of a dermatological treatment or a treatment in the sense of care cosmetics. However, they can also be used in make-up products in decorative cosmetics.

For application in the usual way for cosmetics and dermatics, the preparations according to the invention are applied in sufficient amount on the skin and/or the hair.

In another aspect the invention relates to a cosmetic method for the
i) prevention, treatment or reduction of cellulite,
and/or
(ii) for the
inhibition of the differentiation of preadipocytes,
and/or
inhibition of lipogenesis in adipocytes,
and/or
reduction of the amount of lipids contained in subcutaneous fatty tissue,
characterized by the following step:
application of a wood extract according to the invention or to be used according to the invention, a mixture according to the invention or a preparation according to the invention, in each case preferably in one of the embodiments characterized as preferable above or hereunder, on the skin, preferably application on the skin in an effective amount.

Moreover, it also possible and is regularly advantageous to combine the wood extract according to the invention or to be used according to the invention with other active substances.

Substances and excipients that a cosmetic, dermatological and/or pharmaceutical preparation according to the invention containing an extract according to the invention can additionally contain are for example:

Preservatives, preferably those mentioned in US 2006/0089413, abrasives, antiacne agents and agents for reduction of sebum, preferably those mentioned in WO 2008/046791, other agents against skin ageing, preferably those mentioned in WO 2005/123101, antibacterial agents, anticellulitis agents, antidandruff agents, preferably those mentioned in WO 2008/046795, anti-inflammatory agents, agents preventing irritation, other anti-irritants (anti-inflammatory, irritation inhibiting and irritation preventing agents), preferably those mentioned in WO 2007/042472 and US 2006/0089413, antimicrobial agents, preferably those mentioned in WO 2005/123101, antioxidants, preferably those mentioned in WO 2005/123101, astringents, antiseptics, antistatic agents, binders, buffers, carriers, preferably those mentioned in WO 2005/123101, chelating agents, preferably those mentioned in WO 2005/123101, cell stimulants, cleaning agents, care agents, depilatory agents, surface active substances, deodorants and antiperspirants, preferably those mentioned in WO 2005/123101, plasticizers, emulsifiers, preferably those mentioned in WO 2005/123101, enzymes, essential oils, preferably those mentioned in US 2008/0070825, insect repellents, preferably those mentioned in WO 2005/123101, fibers, film-forming agents, fixatives, foaming agents, foam stabilizers, substances for preventing foaming, foam boosters, fungicides, gelling agents and gel-forming agents, preferably those mentioned in WO 2005/123101, hair care products, hair shaping agents, hair straightening agents, moisture regulators (hydrating agents, moisturizers and/or humectants), preferably those mentioned in WO 2005/123101, osmolytes, preferably those mentioned in WO 2005/123101, compatible solutes, preferably those mentioned in WO 01/76572 and WO 02/15686, bleaching agents, strengthening agents, stain removing agents, optical brighteners, impregnating agents, stain-repellent agents, friction reducing agents, lubricants, moisture creams, ointments, clouding agents, plasticizers, covering agents, polish, gloss agents, polymer, preferably those mentioned in WO 2008/046676, powders, proteins and protein hydrolysates, preferably those mentioned in WO 2005/123101 and WO 2008/046676, refatting agents, abrading agents, skin calming agents, skin cleansing agents, skin care agents, skin healing agents (skin repair agents), preferably containing cholesterol and/or fatty acids and/or ceramides and/or pseudoceramides, here preferably those mentioned in WO 2006/053912, skin lightening agents, preferably those mentioned in WO 2007/110415, skin protective agents, skin softening agents, skin cooling agents, preferably those mentioned in WO 2005/123101, skin warming agents, preferably those mentioned in WO 2005/123101, stabilizers, UV-absorbing agents and UV filters, preferably those mentioned in WO 2005/123101, benzylidene-beta-dicarbonyl compounds, preferably those mentioned in WO 2005/107692, alpha-benzoylcinnamic acid nitriles, preferably those mentioned in WO 2006/015954, AhR-receptor antagonists, preferably those mentioned in WO 2007/128723 and WO 2007/060256, detergents, fabric softeners, suspending agents, skin tanning agents, preferably those mentioned in WO 2006/045760, thickening agents, vitamins, preferably those mentioned in WO 2005/123101, oils, waxes and fats, preferably those mentioned in WO 2005/123101, phospholipids, preferably those mentioned in WO 2005/123101, fatty acids (saturated fatty acids, mono- or polyunsaturated fatty acids, α-hydroxy acids, polyhydroxy fatty acids), preferably those mentioned in WO 2005/123101, liquefiers, dyes and color-protecting agents and pigments, preferably those mentioned in WO 2005/123101, anticorrosives, aromas and flavorings and odoriferous substances, preferably those listed in S. Arctander, Perfume and Flavor Chemicals, self-published, Montclair, N.J., 1969 and Surburg, Panten, Common Fragrance and Flavor Materials, 5th edition, Wiley-VCH, Weinheim 2006, in particular those mentioned explicitly in US 2008/0070825, alcohols and polyols, preferably those mentioned in WO 2005/123101, surfactants, preferably those mentioned in WO 2005/123101, animal extracts, yeast extracts, extracts of algae or microalgae, electrolytes, liquefiers, organic solvents, preferably those mentioned in WO 2005/123101, hair growth modulating agents (hair growth promoting or hair growth inhibiting), preferably those mentioned in EP 2168570 and EP 2193785 or silicones and silicone derivatives, preferably those mentioned in WO 2008/046676.

A preferred preparation according to the invention comprises, along with a wood extract according to the invention or to be used according to the invention, additionally one, two, three or a plurality of substances selected from the group consisting of:
lipolysis stimulants, preferably selected from
(b-i) the group of phosphodiesterase inhibitors, and/or
(b-ii) the group of agonists of beta-adrenergic receptors,
the group of other sirtuin activators,
and
the group of UV radiation absorbing agents.

In particular, preparations containing a *Gleditsia* wood extract according to the invention or to be used according to the invention and one or a plurality of lipolysis stimulants, preferably selected from the group of phosphodiesterase inhibitors, and/or the group of agonists of beta-adrenergic receptors, achieve particularly good anti-cellulite efficacy. Cellulite is prevented, treated or reduced particularly effectively by such a preparation through the positive influence of routes (i) through (iii) described above: in particular routes (i) (adipogenesis) and (ii) (lipogenesis) are influenced very beneficially by a wood extract according to the invention or to be used according to the invention and route (iii) by further lipolysis stimulants.

In a preferred embodiment, a preparation according to the invention, in particular for use as an anti-cellulite agent, additionally contains one or a plurality of anti-cellulite active substances of the group of the xanthines, preferably selected from the group of optionally substituted 3,7- or 3,9-dihydro-1H-purine-2,6-diones of formula (Xa):

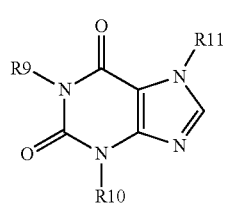

(Xa)

and pharmaceutically acceptable salts thereof, wherein R9, R10 and R11, independently of one another, denote hydrogen or methyl.

The xanthines, in particular those of formula (Xa), can preferably be used as pure substances or also in the form of plant extracts.

The methylxanthines caffeine (R9=R10=R11=CH$_3$), theobromine (R9=H, R10=R11=CH$_3$) and theophylline (R9=R10=CH$_3$, R11=H) are preferred, the xanthine most preferred in the sense of the present invention is caffeine. The theophylline derivative aminophylline is also preferred.

Particularly preferably, a cosmetic, preferably topical, preparation according to the invention contains one or a plurality of compounds of formula (Xa), once again preferably caffeine. The total amount of compounds of formula (Xa) is preferably 0.005-10 wt. %, preferably 0.05-5 wt. %, particularly preferably 0.5-2.5 wt. %, in each case relative to the total weight of the preparation, not including any counter-ions of the compounds of formula (Xa).

Preparations that are also preferred contain combinations of *Gleditsia* wood extract according to the invention or to be used according to the invention with an agonist of beta-adrenergic receptors of the adipocytes.

Preferred agonists of beta-adrenergic receptors are β-phenylethylamines of formula (PhEA) or a pharmaceutically acceptable salt of a compound of formula (PhEA)

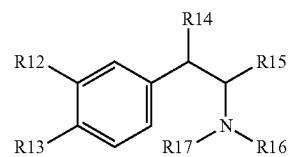

(PhEA)

wherein
R12 and R13, independently of one another, denote hydrogen, hydroxy or methoxy,
R14 denotes hydrogen, hydroxy or methyl,
R15 denotes hydrogen or methyl,
R16 and R17, independently of one another, denote hydrogen or C$_1$-C$_4$-alkyl.

The β-phenylethylamines of formula (PhEA) can preferably be used as pure substances, in the form of their respective hydrochlorides or in the form of plant extracts.

Preferred agonists of beta-adrenergic receptors are adrenaline, noradrenaline, metanephrine, macromerine, normacromerine, hordenine, N-methyltyramine, dopamine, octopamine, tyramine, 2-phenylethylamine, phenylethanolamine, epinine (N-methyldopamine), synephrine, ephedrine, pseudoephedrine, norephedrine and isoprenaline.

Some of these compounds have already been studied in the literature for their activity with respect to the beta-3-adrenergic receptor in human fat cells and of mammals (Naunyn-Schmiedeberg's Archives of Pharmacology 1999, 359, 310-321).

Compounds of formula (PhEA) are preferred in which R17=H and R16 denotes hydrogen or C$_1$-C$_4$-alkyl, preferably hydrogen, methyl or iso-propyl. Compounds of formula (PhEA) in which additionally R15=H are even more preferred.

In another preferred embodiment, the agonists of beta-adrenergic receptors are those compounds in which R12 and R17=H.

Particularly preferred agonists of beta-adrenergic receptors correspond to the formula (PhEA-i), or a pharmaceutically acceptable salt of such a compound, and once again those preferred are tyramine, N-methyltyramine, octopamine, and synephrine and pharmaceutically acceptable salts thereof

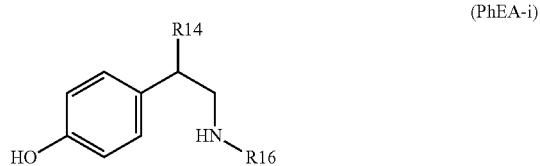
(PhEA-i)

wherein the residues R14 and R16 have the aforementioned (preferred) meaning.

The most preferred agonist of a beta-adrenergic receptor is synephrine (R14=OH, R16=CH$_3$ in formula (PhEA-i)), preferably racemic or enantiomerically pure, and once again the (−)-form is preferred. Synephrine-containing extracts, for example orange blossom extract, are also particularly preferred.

Preferably a cosmetic, preferably topical, preparation according to the invention contains an agonist of a beta-adrenergic receptor, here preferably synephrine, preferably in a total amount of 0.0001-0.10 wt. %, preferably 0.001-0.05 wt. %, even more preferably 0.002-0.02 wt. %, in each case relative to the total weight of the preparation, wherein in the case of salts, the counter-ion of the agonist is not included in the calculation.

Particular advantages are offered by cosmetic, dermatological and pharmaceutical preparations that contain an extract according to the invention and one, two, three or a plurality of further sirtuin activators. Advantageous sirtuin activators are for example resveratrol, resveratrol derivatives, in particular hydroxyresveratrol and resveratrol phosphates such as resveratrol triphosphate, butein, piceatannol, isoliquiritigenin, quercetin, deoxyrhapontin, rhapontin, trihydroxychalcone, pentahydroxychalcone, chalcone, tetrahydroxyflavone, dihydroxyflavone, kaempferol, hydroxyapigenin, apigenin, myrecitin, gossypetin, morin, daidzein, genistein, naringenin, catechin, epicatechin, gallocatechin, epigallocatechin, hinokitiol, ergothioneine, ambroxol, trolox, dipyridamole, camptothecin, coumestrol, pinosylvin, SIRT1 activators as described in US 2005/0136537, isonicotinamide, epsilon-viniferin, Prosveltyl (Silab) containing *Nelumbo nucifera* leaf extract, Longevicell (Silab) containing hydrolyzed *Myrtus communis* leaf extract, Sepivinol (Seppic) containing polyphenols from wine, Orsirtine (ISP Vincience) containing *Oryza sativa* (rice) extract, peptides, in particular *Kluyveromyces* peptides, Dynachondrine ISR (ISP Vincience) containing hydrolyzed soya protein, Sirpetide (ISP Vincience) containing heptapeptides-6, a synthetic peptide containing asparagine, aspartic acid, glutamic acid, glycine, leucine and tyrosine, Matrispondin (Sederma SAS) containing palmitoyltetrapeptide-10 (a synthetic peptide consisting of lysine, threonine and phenylalanine), ACB Sirtuin Complex (Active Concepts) containing *Saccharomyces/Podophyllum peltatum* ferment filtrate, silibinin, milk thistle extracts containing silibinin, *Trigonella foenum graecum* extract, yeast extract, *Echinacea purpurea* extract or pressed must, dicaffeic acid derivatives such as chicoric acid, isochlorogenic acids (e.g. 4,5-dicaffeoylquinic acid) and dicaffeic acid derivative-containing extracts and *Hydrangea arborescens* root extract.

As both skin ageing and the development of cellulite are also associated with degradation of the connective tissue, preferred preparations according to the invention containing a *Gleditsia* wood extract according to the invention or to be used according to the invention can also contain active substances that prevent degradation of the connective tissue. Active substances that inhibit matrix metalloproteinases are advantageous. These enzymes are capable of proteolytic degradation of macromolecules of the extracellular matrix (ECM)/of the connective tissue, which also includes the collagens. In particular, matrix metalloproteinase-1 (MMP-1), matrix metalloproteinase-2 (MMP-2) and matrix metalloproteinase-9 (MMP-9) are responsible for the degradation of the connective tissue of the skin. Inhibition of MMPs is possible for example by adding ursolic acid, retinyl palmitate, propyl gallate, precocene, 6-hydroxy-7-methoxy-2,2-dimethyl-1(2H)-benzopyran, 3,4-dihydro-6-hydroxy-7-methoxy-2,2-dimethyl-1(2H)-benzopyran. Addition of peptides that inhibit MMPs, to preparations according to the invention is advantageous for inhibition of MMPs. Proteins or glycoproteins from soya and hydrolyzed proteins from rice, pea or lupin also inhibit MMPs and are therefore a suitable addition. A combination with a plant extract that inhibits MMPs is also advantageous. We may mention for example an extract from shiitake mushrooms. Combination with extracts from the leaves of the family Rosaceae, subfamily Rosoideae, is also advantageous. The use of blackberry leaf extract, in particular as described in WO 2005/123101 A1, is quite particularly advantageous.

In the context of the present invention, MMP inhibitors that are preferred for use in combination are retinyl palmitate, propyl gallate, precocene, 6-hydroxy-7-methoxy-2,2-dimethyl-1(2H)-benzopyran, 3,4-dihydro-6-hydroxy-7-methoxy-2,2-dimethyl-1(2H)-benzopyran, benzamidine hydrochloride, the cysteine proteinase inhibitors N-ethylmaleimide and epsilon-amino-n-caproic acid, the serine protease inhibitor: phenylmethylsulphonyl fluoride, collhibin (from Pentapharm; INCI: hydrolyzed rice protein), oenotherol (from Soliance; INCI: propylene glycol, aqua, *Oenothera biennis* root extract, ellagic acid and ellagitannins, e.g. from pomegranate), phosphoramidone hinokitiol, EDTA, galardin, EquiStat (from Collaborative Group; apple fruit extract, soya seed extract: ursolic acid, soya isoflavones & soya proteins), sage extracts, MDI (from Atrium; INCI: glycosaminoglycans), Fermiskin (from Silab/Mawi; INCI: Water and *Lentinus Edodes* Extract), Actimp 1.9.3. (from Expanscience/Rahn; INCI: Hydrolyzed Lupine Protein), Lipobelle soya glycones (from Mibelle; INCI: Alcohol, Polysorbate 80, Lecithin and Soy Isoflavones), extracts from green and black tea and numerous other plant extracts, which are listed in WO 02/069992 (see Tables 1-12 there).

In order to counteract the degradation of the connective tissue, furthermore in preferred cosmetic preparations according to the invention containing a *Gleditsia* wood extract according to the invention or to be used according to the invention, combination with active substances that promote the formation of collagen in the tissue is advantageous. Individual substances often used for increasing collagen synthesis are for example active substances such as ascorbic acid and derivatives thereof, retinol and derivatives of retinol or plant extracts such as extracts from *aloe* and *Centella* species. Furthermore, frequently used active substances that increase collagen synthesis also include peptide substances and derivatives thereof, for example carnitine, carnosine, creatine, matrikine peptides (e.g. lysyl-threonyl-threonyl-lysyl-serine) and other peptide structures such as palmitoylated pentapeptides (e.g. Matrixyl, from Sederma) or the oligopeptide with the trade name Vincipeptide (from Vincience/France). Moreover, compounds such as asiatic acid, madecassic acid, madecassoside, asiaticoside, extracts from *Centella asiatica*, niacinamide, astaxanthin, glucanes e.g. from yeasts and oat, soya extracts and soya isoflavones such as genistein and daidzein, rutin, chrysin, morin, betel nut alkaloids, forskolin, betulinic acid, extracts from *Plantago* species, TGF-beta, extracts from *Ginkgo biloba*, glutamine and glycolic acid find application as stimulators of collagen synthesis. Addition of a combination of *Aloe vera* extract, raspberry leaf extract and magnesium ascorbyl phosphate is particularly preferred.

Furthermore, preferred preparations according to the invention containing a *Gleditsia* wood extract according to the invention or to be used according to the invention further comprise additionally (i) coenzyme A for promoting the transport of free fatty acids in the mitochondria and/or (ii) L-carnitine for promoting beta-oxidation.

Therefore the present invention further relates to a preparation, preferably in one of the embodiments characterized as preferable, further containing one or a plurality of matrix metalloproteinase inhibitors,
and/or
one or a plurality of collagen synthesis stimulators,
and/or
coenzyme A and/or L-carnitine.

Particular advantages are also offered in particular by cosmetic and dermatological preparations according to the invention, which contain an extract according to the invention and additionally act as sunscreen agent. Advantageously, these preparations contain at least one UVA filter and/or at least one UVB filter and/or at least one inorganic pigment. The preparations can be in various forms, such as are for example usually employed for sunscreen preparations. Thus, they can for example form a solution, an emulsion of the water-in-oil (W/O) type or of the oil-in-water (O/W) type, or a multiple emulsion, for example of the water-in-oil-in-water (W/O/W) type, a gel, an aqueous dispersion, a solid stick or also an aerosol.

Preparations according to the invention in the area of cosmetics and dermatics, which contain an extract according to the invention, are particularly advantageously combined with substances that absorb or reflect UV radiation, in particular for cosmetic or skin protecting purposes, wherein the total amount of the filter substances is from 0.01 wt. % through 40 wt. %, preferably 0.1% through 20 wt. %, in particular 1.0 through 10 wt. %, relative to the total weight of the preparations, in order to provide cosmetic preparations that protect the hair or the skin from ultraviolet radiation. Advantageously these preparations contain at least one UVA filter and/or at least one UVB filter and/or at least one inorganic pigment, so that a sun protection factor (SPF) of at least >2 (preferably >5) is achieved. These preparations according to the invention can be in various forms, such as are for example usually employed for sunscreen preparations. Thus, they can for example be in the form of a solution, an emulsion of the water-in-oil (W/O) type or of the oil-in-water (O/W) type, or a multiple emulsion, for example of the water-in-oil-in-water (W/O/W) type, a gel, an aqueous dispersion, a solid stick or also an aerosol.

Advantageous UV filters and inorganic light protection pigments are mentioned in WO 2005/123101. UV absorbers particularly suitable for combination are also mentioned in WO 2005/123101.

Advantageous inorganic light protection pigments are finely divided metal oxides and metal salts, which are also mentioned in WO 2005/123101. The total amount of inorganic pigments, in particular hydrophobic inorganic micropigments in the finished cosmetic or dermatological formulations is advantageously in the range from 0.1 through 30 wt. %, preferably 0.1 through 10 wt. %, in particular 0.5 through 6 wt. %, relative to the total weight of the formulations.

Furthermore, it is advantageous to combine the extract according to the invention in cosmetic or dermatological preparations with active substances that penetrate into the skin and protect the skin cells from inside against sunlight-induced damaging effects such as skin ageing, skin inflammation and skin cancer. Preferred active substances in this connection are so-called arylhydrocarbon-receptor antagonists as described in WO 2007/128723. 2-Benzylidene-5,6-dimethoxy-3,3-dimethylindan-1-one is particularly preferred.

Particular advantages are moreover offered by cosmetic or dermatological preparations that contain an extract according to the invention and additionally one, two, three or a plurality of stimulators of glycosaminoglycan (GAG) synthesis. Advantageous GAG synthesis stimulators are for example hyaluronic acid, SymVital (Symrise, INCI: *Aloe Barbadensis* leaf juice powder, Magnesium Ascorbyl Phosphate, *Rubus idaeus* (Raspberry) leaf extract), Subliskin (Sederma, INCI: *Sinorhizobium Meliloti* Ferment Filtrate, Cetyl Hydroxyethylcellulose, Lecithin), Hyalufix (BASF, INCI: Water, Butylene Glycol, *Alpinia galanga* leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetylglucosamine, retinoids, preferably retinol and vitamin A, *Arctium lappa* fruit extract, *Eriobotrya japonica* extract, genkwanin, N-methyl-L-serine and soya protein hydrolysate.

Preferred cosmetic or pharmaceutical preparations contain, in addition to the extract according to the invention, additionally one, two, three or a plurality of proteasome activators. Advantageous proteasome activators are e.g. *Phaeodactylum tricornutum*, palmitoyl isoleucine, *Olea europaea* leaf extract, oleuropein, hydrolyzed *Candida saitoana* extract (Silab) and plankton extract from Scenedesmus of Sahel (Biotech Marine).

According to the invention, the cosmetic and pharmaceutical preparations optionally comprise one, two, three, four or a plurality of further anti-inflammatory active compounds. All active substances that reduce skin irritation and/or reddening of the skin that are suitable for cosmetic and/or dermatological uses or are usual can be used. However, combinations with one, two, three, four or a plurality of further anti-inflammatory effective compounds, selected from the group of the following compounds, are particularly preferred: steroidal anti-inflammatory substances of the corticosteroid type, preferably hydrocortisone, hydrocortisone derivatives such as hydrocortisone-17-butyrate, dexamethasone, dexamethasone phosphate, methylprednisolone or cortisone and other steroidal anti-inflammatory drugs; non-steroidal anti-inflammatory drugs, preferably oxicams such as piroxicam or tenoxicam; salicylates such as aspirin, disalcid, solprin or fendosal; acetic acid derivatives such as diclofenac, fenclofenac, indomethacin, sulindac, tolmetin, or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone; natural anti-inflammatory substances or substances alleviating reddening and/or pruritus, preferably plant extracts, special highly effective plant extract fractions and high-purity active substances isolated from plant extracts, particularly preferably extracts, fractions and active substances from chamomile, ginger, *Aloe vera, Commiphora* species, liquorice (*Glycyrrhiza*) species such as *Glycyrrhiza glabra* and *Glycyrrhiza inflata, Rubia* species, willow, willow-herb, oat, *calendula*, arnica, St. John's Wort, honeysuckle, rosemary, balm, *Passiflora incarnata, hamamelis, Pueraria, dianthus* or *echinacea* and isolated pure substances therefrom, preferably bisabolol, apigenin, apigenin-7-glucoside, rosmarinic acid, Boswellia acid, phytosterols, glycyrrhizine, glabridin, licochalcone A and anthranilic acid amides such as in particular avenanthramides or dianthramides; naturally occurring anthranilic acid derivatives, preferably from oats or clove (*Dianthus* species); anthranilic acid amides produced completely synthetically or partially synthetically, preferably dihydroavenanthramide D (Symrise AG); naturally occurring ingredients of liquorice and/or compounds produced completely synthetically or partially synthetically, preferably tetrahydrolicochalcone A and the compounds mentioned in WO 2005/123101.

The amount of the anti-irritants (one or a plurality of compounds) in the preparations according to the invention is preferably 0.0001 through 20 wt. %, particularly preferably 0.0001-10 wt. %, in particular 0.001-5 wt. %, relative to the total weight of the preparation.

The one or the plurality of further substances with physiological cooling action, which can be used as a constituent in a cosmetic, dermatological and/or pharmaceutical preparation according to the invention, are preferably selected from the following list: menthol and menthol derivatives (e.g. L-menthol, D-menthol, racemic menthol, isomenthol, neoisomenthol, neomenthol) menthyl ethers (e.g. (I-menthoxy)-1,2-propanediol, (I-menthoxy)-2-methyl-1,2-propanediol, I-menthyl-methyl ether), menthyl esters (e.g. menthyl formate, menthyl acetate, menthyl isobutyrate, menthyl lactates, L-menthyl-L-lactate, L-menthyl-D-lactate, menthyl-(2-methoxy)acetate, menthyl-(2-methoxyethoxy)acetate, menthyl pyroglutamate), menthyl carbonates (e.g. menthyl propylene glycol carbonate, menthyl ethylene glycol carbonate, menthyl glycerol carbonate or mixtures thereof), the semi-esters of menthols with a dicarboxylic acid or derivatives thereof (e.g. mono-menthyl succinate, mono-menthyl glutarate, mono-menthyl malonate, O-menthyl succinic acid ester-N,N-(dimethyl)amide, O-menthyl succinic acid ester amide), menthanecarboxylic acid amides (preferably menthanecarboxylic acid-N-ethylamide [WS3] or $N^\alpha$-(menthanecarbonyl)glycine ethyl ester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005/049553, menthanecarboxylic acid-N-(alkoxyalkyl)amides), menthone and menthone derivatives (e.g. L-menthone glycerolketal), 2,3-dimethyl-2-(2-propyl)-butanoic acid derivatives (e.g. 2,3-dimethyl-2-(2-propyl)-butanoic acid-N-methylamide [WS23]), isopulegol or its esters (I-(−)-isopulegol, I-(−)-isopulegol acetate), menthane derivatives (e.g. p-menthane-3,8-diol), cubebol or synthetic or natural mixtures containing cubebol, pyrrolidone derivatives of cycloalkyldione derivatives (e.g. 3-methyl-2(1-pyrrolidinyl)-2-cyclopenten-1-one) or tetrahydropyrimidin-2-ones (e.g. icilin or related compounds, as described in WO 2004/026840).

The or the plurality of further substances with physiological cooling action that can be used as a constituent of a cosmetic, dermatological and/or pharmaceutical preparation according to the invention are in particular preferably substances that produce at least substantially a physiological cooling action. Preferred substances of this kind are: menthyl ethers (e.g. (I-menthoxy)-1,2-propanediol, (I-menthoxy)-2-methyl-1,2-propanediol), more polar menthyl esters (e.g. menthyl lactates, L-menthyl-L-lactate, L-menthyl-D-lactate, menthyl-(2-methoxy)acetate, menthyl-(2-methoxyethoxy)acetate, menthyl pyroglutamate), menthyl carbonates (e.g. menthyl propylene glycol carbonate, menthyl ethylene glycol carbonate, menthyl glycerol carbonate), the semi-esters of menthols with a dicarboxylic acid or derivatives thereof (e.g. mono-menthyl succinate, mono-menthyl glutarate, mono-menthyl malonate, O-menthyl succinic acid ester-N,N-(dimethyl)amide, O-menthyl succinic acid ester amide), menthanecarboxylic acid amides (e.g. menthanecarboxylic acid-N-ethylamide [WS3], $N^\alpha$-(menthanecarbonyl)glycine ethyl ester [WS5], menthanecarboxylic acid-N-(4-cyanophenyl)amide, menthanecarboxylic acid-N-(alkoxyalkyl)amides), menthone derivatives (e.g. L-menthone glycerol ketal), 2,3-dimethyl-2-(2-propyl)-butanoic acid derivatives (e.g. 2,3-dimethyl-2-(2-propyl)-butanoic acid-N-methylamide), pyrrolidone derivatives of cycloalkyldione derivatives (e.g. 3-methyl-2(1-pyrrolidinyl)-2-cyclopenten-1-one) or tetrahydropyrimidin-2-ones (e.g. icilin or related compounds, which are described in WO 2004/026840).

Components that produce a sensation of heat, sharpness, formication or tingling on the skin or on the mucosae, in particular flavoring substances with a heat generating effect and/or sharp-tasting compounds (spicy substances), which can be a constituent of a preparation according to the invention along with a *Gleditsia* wood extract according to the invention or to be used according to the invention, are mentioned in WO 2005/123101.

In some preparations, a combination with (metal) chelating agents may also be advantageous. The compounds stated in WO 2005/123101 are (metal) chelating agents whose use is preferred.

The *Gleditsia* wood extracts according to the invention or to be used according to the invention can also be used in cosmetic and dermatological preparations advantageously in combination with insect repellents such as DEET, IR 3225, Dragorepel (Symrise GmbH & Co. KG).

The *Gleditsia* wood extracts according to the invention or to be used according to the invention can moreover be used in cosmetic and dermatological preparations advantageously in combination with hair care products and antidandruff active substances (e.g. climbazole, ketoconazole, piroctone olamine, zinc-pyrithione).

The *Gleditsia* wood extracts according to the invention or to be used according to the invention can also be used in many cases advantageously in combination with one or a plurality of preservatives in preparations according to the invention. The preservatives mentioned in WO 2005/123101 are preferably selected.

In addition to a *Gleditsia* wood extract according to the invention or to be used according to the invention, preparations according to the invention can also contain further plant extracts usable for cosmetic purposes. Preferably the plant extracts are selected from the substances listed in the table beginning on page 44 of the 3rd edition of the manual for ingredients declaration of cosmetic products, published by the "Industrial Association for Body Care Products and Detergents (Industrieverband Körperpflegemittel and Waschmittel e.V. (IKW)), Frankfurt. The extracts mentioned in particular in WO 2005/123101 are also advantageous.

Cosmetic preparations that contain a *Gleditsia* wood extract according to the invention or to be used according to the invention can, in particular when crystalline or microcrystalline solids such as for example inorganic micropigments are to be incorporated in the preparations, also contain according to the invention, anionic, cationic, non-ionic and/or amphoteric surfactants mentioned in WO 2005/123101.

The surface active substance can be present in the preparations according to the invention in a concentration between 1 and 98 wt. %, relative to the total weight of the preparations.

The oil phase of a preparation according to the invention containing a *Gleditsia* wood extract according to the invention or to be used according to the invention can advantageously be selected from the groups of substances mentioned in WO 2005/123101.

Preparations according to the invention are also advantageous that are administered orally, e.g. in the form of tablets (e.g. film-coated tablets), coated tablets, capsules (e.g. gelatin capsules), granules, juices, solutions, emulsions, microemulsions, sprays or in some other form of orally consumable products or in the form of foodstuffs.

The invention further relates to a wood extract according to the invention, preferably in one of the embodiments characterized as preferable, and a mixture according to the invention, preferably in one of the embodiments characterized as preferable, for use in a method or for use for the prevention, treatment and/or reduction of cellulite.

The invention also relates to a wood extract according to the invention or to be used according to the invention, preferably in one of the embodiments characterized as preferable, a mixture according to the invention, preferably in one of the embodiments characterized as preferable, and a preparation according to the invention, preferably in one of the embodiments characterized as preferable, as a medicinal product.

As already pointed out above, the *Gleditsia* wood extracts according to the invention or to be used according to the invention, preferably in the embodiments characterized as preferable, additionally display a SIRT-stimulating, i.e. SIRT-activating, efficacy, in particular with respect to SIRT1. Owing to their SIRT-stimulating properties, the *Gleditsia* wood extracts according to the invention or to be used according to the invention also act as active substances for the prevention, treatment and/or reduction of ageing, in particular skin ageing, for improvement of the stress response and prevention, decrease and/or repair of stress-induced damage and/or for attaining a uniform skin tone.

As already pointed out above, the *Gleditsia* wood extracts according to the invention or to be used according to the invention, preferably in the embodiments characterized as preferable, additionally display anti-irritant efficacy. Owing to their anti-inflammatory properties, in particular with respect to inhibition of COX-2 activity, the *Gleditsia* wood extracts according to the invention or to be used according to the invention also act as active substances for the prevention, treatment and/or reduction of skin irritation and skin inflammation and/or for attaining a uniform skin tone.

The term "skin", in the context of this invention, in connection with the SIRT-stimulating and/or the anti-irritant efficacy of a *Gleditsia* wood extract according to the invention or to be used according to the invention, also comprises "mucous membrane" (mucosa), in particular the mucous membrane of the mouth, gums, throat, pharynx, nose, respiratory tract and gastrointestinal tract.

In addition to cosmetic and dermatological uses, SIRT activators can also be used as pharmaceutical (therapeutic) active substances. Diseases such as chronic and degenerative diseases, cardiovascular diseases, malignant neoplasms, liver diseases, diabetes mellitus, arthritis, inflammatory diseases and Alzheimer's disease increase with age. Recent studies link sirtuins and in particular SIRT1 with many of these age-related diseases.

Thus, it has been shown for age-related heart diseases that the overexpression of SIRT1 leads for example to a decrease in cardiac hypertrophy, apoptosis, fibrosis, cardiac dysfunction and the expression of senescence markers. SIRT also supports cardiac function indirectly through deacetylation of the eNOS enzyme.

SIRT1 can furthermore mobilize fat reserves of the body through suppression of the PPAR-gamma receptor. This effect, together with low insulin production, increased insulin sensitivity and insulin growth factor 1 (IGF-1), can delay the onset of age-related diseases associated with obesity, e.g. diabetes.

SIRT1 apparently also plays a role in Alzheimer's disease, by controlling the production of β-amyloid, which forms the plaques typical of Alzheimer's.

The invention is explained in more detail below, on the basis of examples. The examples serve to illustrate the invention, without restricting the scope of protection of the patent claims. Unless stated otherwise, all information given refers to weight.

EXAMPLE 1

Laboratory-Scale Production of Honey Locust Heartwood Extracts

For production of the wood extracts according to the invention, the respective extractants stated in Table 1.1 below were added, in each case in the stated proportions, to wood raspings from Honey locust (*Gleditsia triacanthos*) heartwood (batch 1 or 2 from two different tree trunks) and extraction was performed for 2 h under reflux at ambient (laboratory) pressure. Then the mixture was cooled, filtered and the extractant or extractants and water were removed completely under vacuum, so that a dry extract was obtained.

TABLE 1.1

Honey locust (*Gleditsia triacanthos*) heartwood extracts according to the invention

| Test sample | Extractant | Wood batch | Weight ratio wood raspings:extractant | Yield of dry extract [wt. %] |
|---|---|---|---|---|
| BIO2162 | Water | 2 | 1:12 | 3.3 |
| BIO2162/1 | Water | 1 | 1:17 | 3.4 |
| BIO781/1 | Ethanol/water 1:1 (w/w) | 2 | 1:8 | 5.9 |
| BIO781/2 | Ethanol/water 1:1 (w/w) | 1 | 1:21 | 6.2 |
| BIO2163 | Ethanol | 2 | 1:12 | 2.8 |
| BIO2163/1 | Ethanol | 1 | 1:17 | 2.3 |
| BIO792 | Ethyl acetate | 1 | 1:21 | 1.0 |
| BIO796 | Acetone | 1 | 1:16 | 2.3 |

The extracts are characterized by HPLC-fingerprint analysis and quantitative determination of the content of fisetin (3,3',4',7-tetrahydroxyflavone) and fustin (3,3',4',7-tetrahydroxyflavanone).

HPLC column: YMC ODS-AQ, 5 µm, 150×3 mm with precolumn, temperature: 40° C., flow: 0.6 ml/min, acetonitrile/water with 0.1% formic acid gradient, injection volume: 5 µl, detection wavelengths: 232 and 280 nm

TABLE 1.2

Content (based on the dry extract) of fisetin and
fustin in various Honey locust heartwood extracts

| Test sample | Extractant | Wood batch | Fisetin content [wt. %] | Fustin content [wt. %] |
|---|---|---|---|---|
| BIO2162 | Water | 2 | Not detectable | 5.3 |
| BIO2162/1 | Water | 1 | Not detectable | 0.9 |
| BIO781/1 | Ethanol/water 1:1 (w/w) | 2 | 0.9 | 11.1 |
| BIO781/2 | Ethanol/water 1:1 (w/w) | 1 | 1.0 | 1.5 |
| BIO2163 | Ethanol | 2 | 1.8 | 17.4 |
| BIO2163/1 | Ethanol | 1 | 2.1 | 3.5 |
| BIO792 | Ethyl acetate | 1 | 2.4 | 1.8 |
| BIO796 | Acetone | 1 | 4.7 | 1.4 |

EXAMPLE 1A

Industrial-Scale Production of a *Gleditsia* Wood Extract According to the Invention Wood raspings of *Gleditsia triacanthos* were extracted in a strainer basket extractor with the extractant=EtOH/water 1:1 (w/w) (weight ratio wood raspings:extractant=1:7) for a period of 2 h under reflux. The resultant first extract was separated and the wood was extracted for a second time under the same conditions. The two extracts obtained were combined and then concentrated by distillation, so that the aqueous product obtained was largely free from ethanol (the corresponding dry extract content of the resultant product was approx. 7.5 wt. %).

EXAMPLE 1B

Preparation of a Mixture According to the Invention

| | |
|---|---|
| 1,2-Propylene glycol | 60 wt. % |
| Water | to 100 wt. % |
| *Gleditsia triacanthos* heartwood extract from example 1A | 3 wt. % |
| Sodium benzoate | 0.5 wt. % |
| Potassium sorbate | 0.2 wt. % |
| Lactic acid for adjusting the pH value to 4.5 | |

The product from example 1A was mixed with propylene glycol, water, sodium benzoate and potassium sorbate in the respective amounts stated and the pH value of this mixture was adjusted to a value of 4.5 (measured at 25° C.), so that a mixture according to the invention with the above composition was obtained. After standing for 5 days, the mixture was filtered.

EXAMPLE 2

Adipogenesis Assay

3T3-L1 cells (mouse embryonic fibroblast-like adipocyte cell line) are seeded in a 48-well plate with collagen I coating at a concentration of $3 \times 10^4$ cells/well. After culture for 72 h at 37° C. and 5% $CO_2$ in DMEM (Dulbecco's Modified Eagle's Medium), enriched with 10% calf serum, various concentrations of the test samples are added to DMEM, enriched with 10% fetal calf serum supplemented with 1 µg/ml insulin, 0.25 µM dexamethasone and 0.5 mM IBMX (3-isobutyl-1-methylxanthine), and incubated for a further 48 h. The medium is changed, applying DMEM, enriched with 10% fetal calf serum supplemented with 1 µg/ml insulin. After further cultivation for 48 h, the medium is changed again, applying DMEM enriched with 10% fetal calf serum.

After incubation for a further 72 h, the intracellularly stored lipids are quantified as a measure for the differentiation of the cells, by measuring the fluorescence after staining the lipids with the fluorescent dye Nile Red.

The inhibition of adipogenesis in the presence of the test samples is calculated from the following equation:

$$\text{Inhibition of adipogenesis [\%]} = 100 - \left( \frac{RFU \text{ Test substance} - RFU \text{ Control without cells}}{RFU \text{ Control} - RFU \text{ Control without cells}} \times 100 \right)$$

with
RFU test substance=relative fluorescence units of the wells with test substance and with cells
RFU control=relative fluorescence units of the wells without test substance, but with cells
RFU control without cells=relative fluorescence units of the wells without test substance and without cells.

$IC_{50}$ is calculated from the adipogenesis inhibition [%] in a series of dilutions of samples tested. This is the concentration at which adipogenesis is inhibited 50%.

TABLE 2.1

Adipogenesis inhibition of different Honey locust heartwood extracts (mean values from at least 2 independent tests)

| Test sample | $IC_{50}$ [%] |
|---|---|
| BIO781/2 | 0.011 |
| BIO792 | 0.006 |

The extracts show definite inhibition of adipogenesis.
In order to investigate the influence of the two ingredients fustin and fisetin identified, these were tested in parallel with the extract at the concentration corresponding to their content in the extract.

TABLE 2.2

Adipogenesis inhibition of Honey locust heartwood extract BIO781/2 and the two substances fustin and fisetin contained therein

| Test sample | Content in BIO781/2 [wt. %] | Test concentration [%] | Adipogenesis inhibition [%] |
|---|---|---|---|
| BIO781/2 | | 0.03 | 40 |
| Fustin | 1.5 | 0.0005 | No inhibition |
| Fisetin | 1.0 | 0.0003 | No inhibition |

The results show that fustin and fisetin do not show any activity in the concentration tested and therefore are not responsible for the adipogenesis inhibiting action of the extract BIO78112.

EXAMPLE 3

Lipogenesis Assay

Lipogenesis is to be understood as the storage of triglycerides in adipocytes. This storage can be inhibited through inhibition of the activity of extracellular lipoprotein lipase (LPL), in that the hydrolysis of extracellular triglycerides and as a result the uptake of free fatty acids by adipocytes is reduced. The inhibition of pancreatic lipase (PL) is investigated as a preliminary test.

Methylumbelliferyl oleate (MUF-oleate) is added as substrate to PL (Sigma-Aldrich) in the presence of test substances used in different concentrations. Through hydrolysis of the MUF-oleate by PL, there is formation of fluorescent methylumbelliferone (MUF), which is quantified. Inhibition of the hydrolysis of MUF-oleate is a measure for inhibition of the activity of PL.

$$\text{Inhibition of } PL[\%] = 100 - \left( \frac{MUF \text{ Test substance} - MUF \text{ Control without } PL}{MUF \text{ Control} - MUF \text{ Control without } PL} \times 100 \right)$$

with
MUF test substance=MUF concentration of the wells with test substance and with PL
MUF control=MUF concentration of the wells without test substance, but with PL
MUF control without PL=MUF concentration of the wells without test substance and without PL.

$IC_{50}$ is calculated from the inhibition of PL [%] in a series of dilutions of samples tested. This is the concentration at which the activity of PL is inhibited 50%.

TABLE 3

Inhibition of PL by different Honey locust heartwood extracts

| Test sample | $IC_{50}$ [%] |
|---|---|
| BIO781/2 | 0.054 |
| BIO792 | 0.012 |
| BIO796 | 0.013 |

The extracts show a definite inhibition of lipase activity.

EXAMPLE 4

SIRT1 Assay

NHDF cells (normal human dermal fibroblasts) are seeded in a 96-well microtitre plate. The cells are cultured for 24 h at 37° C. and 5% $CO_2$ in DMEM (Dulbecco's Modified Eagle's Medium). Then the test samples are added and the cells are cultured for a further 48 h. After washing the cells with PBS (phosphate-buffered saline), the cells are fixed and permeabilized with paraformaldehyde. Then they are washed once more, blocked with BSA (bovine serum albumin) and incubated with a secondary antibody. After thorough washing, the fluorescence is measured with a microplate reader and fluorescence pictures are taken with a camera coupled to a fluorescence microscope.

The stimulation of SIRT1 protein expression in the presence of the test samples is calculated from the following equation:

$$\text{Stimulation of } SIRT1 \text{ protein expression } [\%] = \left( \frac{RFU \text{ Test sample} - RFU \text{ background}}{RFU \text{ control} - RFU \text{ background}} \times 100 \right) - 100$$

RFU test sample=relative fluorescence units of the wells with test sample, completely stained
RFU control=relative fluorescence units of the wells without test sample, completely stained
RFU background=relative fluorescence units of the wells without test sample, only stained with secondary antibody.

TABLE 4

Stimulation of SIRT1 protein expression by Honey locust wood ethanol/water 1:1 extracts versus control

| Test sample | Concentration [%] | Stimulation [%] |
|---|---|---|
| BIO781/1 | 0.01 | 25 |
| BIO781/2 | 0.01 | 21 |

Both test samples show statistically significant (p<0.05, T-test) stimulation of SIRT1 protein expression. Although the two extracts differ markedly with respect to their fustin content and with respect to their HPLC fingerprints, the stimulating effect on SIRT1 protein expression is comparable.

EXAMPLE 5

Cyclooxygenase-2 (COX-2) Assay

The COX inhibition screening assay from Cayman Chemical Company was used. COX-2 is mixed in the presence of the test samples with the fluorometric substrate 10-acetyl-3,7-dihydroxyphenoxanin (ADHP) and haem. The reaction is started by adding the substrate arachidonic acid.

COX-2 converts the arachidonic acid to prostaglandin endoperoxide G2 (PGG2). Then PGG2 is reduced to the corresponding alcohol PGH2. During this reaction, ADHP converts to the fluorescent resorufin. Resorufin is quantified at an extinction wavelength of 535 nm and an emission wavelength of 590 nm.

Inhibition of COX-2 [%]=100−((Resorufin test sample−Resorufin control without COX-2/Resorufin control−Resorufin control without COX-2)×100)

with
Resorufin test sample=resorufin concentration of the wells with test sample and with COX-2
Resorufin control=resorufin concentration of the wells without test sample, but with COX-2
Resorufin control without COX-2=resorufin concentration of the wells without test sample and without COX-2.

$IC_{50}$ is calculated from the inhibition of COX-2 [%] in a series of dilutions of samples tested. This is the concentration at which the activity of COX-2 is inhibited 50%.

TABLE 5

Inhibition of COX-2 by various Honey locust heartwood extracts

| Test sample | $IC_{50}$ [%] |
|---|---|
| BIO781/2 | 0.0005 |
| BIO781/1 | 0.0011 |
| BIO2162 | 0.0021 |
| BIO2163 | 0.0010 |

All wood extracts showed definite inhibition of COX-2 activity. It can be concluded from the results that fisetin and fustin are not, or are only to a slight extent, responsible for the anti-inflammatory action of the extracts. Thus, on the one hand, extract BIO2162 shows good activity, although fisetin is not detectable, and on the other hand BIO781/1, despite higher fustin content by a factor of 7, displays lower COX-2 inhibiting activity than BIO781/2.

FORMULATION EXAMPLES

| Example No. | Form of product |
| --- | --- |
| 1 | Antidandruff shampoo |
| 2 | Anti-cellulite body oil |
| 3 | After-sun spray O/W |
| 4 | Skin-firming night cream W/O |
| 5 | Antiwrinkle ampoule |
| 6 | After-shave hydrogel |
| 7 | Body peeling |
| 8 | Anti-cellulite balm |
| 9 | Skin lightening day care fluid O/W |
| 10 | Barrier repair cream O/W |
| 11 | Sunscreen lotion SPF 24 (UVA/UVB balance) |

| Ingredients | INCI Name | Wt. % 1 | 2 | 3 | 4 | 5 | 6 |
| --- | --- | --- | --- | --- | --- | --- | --- |
| *Gleditsia triacanthos* Wood Extract, Dried | *Gleditsia triacanthos* Extract | | | | | 0.01 | |
| *Gleditsia triacanthos* Wood Extract (Dry Extract Content 3%) | Propylene Glycol, Water (Aqua), *Gleditsia triacanthos* Extract | | | 3 | | | |
| *Gleditsia triacanthos* Wood Extract (Dry Extract Content 10%) | Maltodextrin, *Gleditsia triacanthos* Extract | 0.1 | | | | | |
| *Gleditsia triacanthos* Wood Extract (Dry Extract Content 1%) | Caprylic/Capric Triglycerides, *Gleditsia triacanthos* Extract | | 5 | | | | |
| A-C Polyethylene 9 A | Polyethylene | | | | | | |
| Actipone Black Coffee GROW | Water (Aqua), Glycerin, *Coffea Arabica* (Coffee) Seed Extract, *Coffea Robusta* Seed Extract | | | | | | |
| Actipone *Laminaria Saccharina* | Glycerin, Water (Aqua), *Laminaria Saccharina* Extract | | | | | | 0.3 |
| Actipone Nutgrass (Motha) Root GROW | Water (Aqua), Glycerin, *Cyperus Rotundus* Root Extract | | | | | | |
| Allantoin | Allantoin | | | | | | 0.1 |
| *Aloe Vera* Gel Conc. 10:1 | *Aloe Barbadensis* Leaf Juice | | | | | | |
| Aluminum Stearate | Aluminium Stearate | | | | 1.2 | | |
| Arbutin | B-Arbutin | | | | | | |
| Arlypon F | Laureth-2 | 2 | | | | | |
| Avocado Oil | *Persea Gratissima* (Avocado) Oil | | 2 | 3 | | | |
| Biotive L-Arginine | Arginine | | | | | | |
| Biotive Esculin Sesquihydrate | Esculin | | | | | | |
| Biotive Troxerutin | Troxerutin | | | | | | |
| (−)-Alpha-Bisabolol Natural | Bisabolol | | | 0.2 | | | |
| Carbopol Ultrez-10 | Carbomer | | | | | | 0.4 |
| Carnitine | Carnitine | | | | | | |
| Ceramidebio | Cetylhydroxyproline Palmitamide | | | | | | |
| Citric Acid 10% In Water | Citric Acid | 0.5 | | | | | |
| Covi-Ox T-70 | Tocopherol | | 0.2 | 0.1 | | | |
| Crinipan AD | Climbazole | 0.3 | | | | | |
| D-Panthenol | Panthenol | 0.5 | | 1 | | 1 | 0.5 |
| Dermacryl AQF | Acrylates Copolymer | | | | | | |
| Dow Corning 200(100 cs) Silicone Fluid | Dimethicone | | | | | | |
| Dow Corning 246 Fluid | Cyclohexasiloxanes, Cyclopentasiloxanes | | | | 2 | | |
| Dracorin 100 S.E.P. | Glyceryl Stearate, PEG-100 Stearate | | | | | | |
| Dracorin CE | Glyceryl Stearate Citrate | | | | | | |
| Dracorin GMS | Glyceryl Stearate | | | | | | |
| Dracorin GOC | Glyceryl Oleate Citrate, Caprylic/Capric Triglyceride | | | | 2 | | |
| Dragocalm | Water (Aqua), Glycerin, *Avena Sativa* (Oat) Kernel Extract | | | | | 1 | |
| Dragocid Liquid | Phenoxyethanol, Methylparaben, | 0.7 | | 0.8 | | | |

| | | | | | | |
|---|---|---|---|---|---|---|
| Dragoderm | Ethylparaben, Butylparaben, Propylparaben, Isobutylparaben Glycerin, *Triticum Vulgare* (Wheat) Gluten, Water (Aqua) | 0.5 | | | | |
| Dragosan W/O P | Sorbitan Isostearate, Hydrogenated Castor Oil, Ceresin, Beeswax (Cera Alba) | | | 8 | | |
| Dragosantol 100 | Bisabolol | | | 0.2 | | 0.1 |
| Dragosine | Carnosine | | | | 0.2 | |
| Dragoxat 89 | Ethylhexyl Isononanoate | | 10 | 7 | | |
| Edeta B Powder | Tetrasodium EDTA | | | | | |
| Edeta BD | Disodium EDTA | | | | | |
| Emulgin B2 | Ceteareth-20 | | | | | |
| Emulsiphos | Potassium Cetyl Phosphate, Hydrogenated Palm Glycerides | | | | | |
| Ethanol | Alcohol Denat. | | | 5 | | 8 |
| Essential Oil | Essential Oil | | 0.2 | | | |
| Extrapone *Aloe Vera* | Water (Aqua), *Aloe Barbadensis*, Propylene Glycol, Alcohol | | | | | 2 |
| Extrapone Butcher's Broom GW P | Glycerin, Water (Aqua), Pentylene Glycol, *Ruscus Aculeatus* Root Extract | | | | | |
| Extrapone *Ginkgo Biloba* | Propylene Glycol, Water (Aqua), *Ginkgo Biloba* Leaf Extract, Glucose, Lactic Acid | | | | | |
| Extrapone Green Tea (Organic) GW | Water (Aqua), Glycerin, *Camellia Sinensis* Leaf Extract | | | | | |
| Extrapone Guarana | Water (Aqua), Propylene Glycol, *Paullinia Cupana* Seed Extract, Alcohol | 0.5 | | | | |
| Extrapone Horse Chestnut | Propylene Glycol, Water (Aqua), *Aesculus Hippocastanum* (Horse Chestnut) Seed Extract, Glucose, Lactic Acid | | | | | |
| Extrapone Ivy | Propylene Glycol, Water (Aqua), *Hedera Helix* (Ivy) Leaf/Stem Extract, Glucose, Lactic Acid | | | | | |
| Extrapone Orange Flower | Water (Aqua), Propylene Glycol, *Citrus Aurantium Amara* (Bitter Orange) Flower Extract | | | | | |
| Extrapone Orange Peel | Water (Aqua), Propylene Glycol, Alcohol, *Citrus Aurantium Dulcis* (Orange) Peel Extract | | | | | |
| Extrapone Seaweed | Water (Aqua), Butylene Glycol, *Fucus Vesiculosus* Extract | | | | | |
| Frescolat MAG | Menthone Glycerin Acetal | | | | 0.1 | |
| Frescolat ML | Menthyl Lactate | 0.2 | 0.5 | | | 0.3 |
| Genapol LRO Liquid | Sodium Laureth Sulphate | 37 | | | | |
| Givobio GZN | Zinc Gluconate | | | | | |
| Glycerol | Glycerin | | 4 | 3 | | |
| Hydrolite 5 | Pentylene Glycol | | 5 | | | 5 |
| Hydroviton-24 | Water (Aqua), Pentylene Glycol, Glycerin, Lactic Acid, Sodium Lactate, Serine, Urea, Sorbitol, Sodium Chloride, Allantoin | | | 1 | | |
| Isoadipate | Diisopropyl Adipate | | | | | |
| Isodragol | Triisononanoin | | 13 | | | |
| Isopropyl palmitate | Isopropyl-Palmitate | | | | | |
| Jojoba Oil | *Simmondsia Chinensis* (Jojoba) Seed Oil | | | 2 | | |
| Jojoba Oil Ethoxylate (Oxypon 328) | Peg-26 Jojoba Acid, Peg-26 Jojoba Alcohol | | | | | |
| Potassium Sorbate | Potassium Sorbate | | | 0.1 | | |
| Karion F | Sorbitol | | | | | |
| Keltrol CG-RD | Xanthan Gum | | | | 0.05 | |
| Koji Acid | Kojic Acid | | | | | |

| | | | | | | | |
|---|---|---|---|---|---|---|---|
| Caffeine | Caffeine | | | | | | |
| Lanette 16 | Cetyl Alcohol | | | | | | |
| Lanette O | Cetearyl Alcohol | | | | | | |
| Lara Care A-200 | Galactoarabinan | | | | | | |
| Magnesium Sulphate | Magnesium Sulfate | | | | 0.7 | | |
| Macadamia Nut Oil | *Macadamia Ternifoia* Seed Oil | | 0.5 | | | | |
| Sea Salt (Dead Sea) | Sea Salt (Maris Sal) | | | | | | |
| Mineral oil | Mineral Oil | | | | 8 | | |
| Sodium ascorbyl phosphate | Sodium Ascorbyl Phosphate | | | | | | |
| Sodium chloride | Sodium Chloride | 0.1 | | | | | |
| Sodium Hydroxide Soln. 10% in Water | Sodium Hydroxide | | | | | | 0.75 |
| Neo Actipone White Tea | *Camellia Sinensis* Leaf Extract | | | | | | |
| Neo Heliopan 303 | Octocrylene | | | | | | |
| Neo Heliopan 357 | Butylmethoxydibenzoylmethane | | | | | | |
| Neo Heliopan AP, 15% solution, neutralized with L-arginine | Aqua, Disodium Phenyl Dibenzimidazole Tetrasulphonate, Arginine | | | | | | |
| Neo Heliopan AV | Ethylhexyl Methoxycinnamate | | | | | | |
| Neo Heliopan BB | Benzophenones-3 | | | | | | |
| Neo Heliopan E 1000 | Isoamyl p. Methoxycinnamate | | | | | | |
| Neo Heliopan HMS | Homosalate | | | | | | |
| Neo Heliopan Hydro, 20% solution, neutralized with Biotive Arginine | Aqua, Phenylbenzimidazole, Sulphonic Acid, Arginine | | | | | | |
| Neo Heliopan OS | Ethylhexyl Salicylate | | | | | | |
| Neo-PCL Water Soluble N | Trideceth-9, PEG-5 Ethylhexanoate, Water (Aqua) | 1.5 | | | | | 1 |
| Neutral oil | Caprylic/Capric Triglyceride | | | 5 | | | |
| Oxynex K Liquid | PEG-8, Tocopherol, Ascorbyl Palmitate, Ascorbic Acid, Citric Acid | | | | | | |
| Ozokerite Wax 2389 | Ozokerite | | | | 2 | | |
| Paraffin oil | Paraffinum Liquidum | | to 100 | | | | |
| Perfume oil | Parfum (Fragrance) | 0.5 | 0.5 | 0.25 | 0.3 | 0.1 | 0.1 |
| PCL-Liquid 100 | Cetearyl Ethylhexanoate | | | 21 | 4 | 5 | |
| PCL-Solid | Stearyl Heptanoate, Stearyl Caprylate | | | | 0.5 | | |
| Pemulen TR-2 | Acrylates/C10-30Alkyl Acrylate Crosspolymer | | | | 0.25 | | |
| Phytoconcentrole Shea Butter | *Glycine Soja* (Soybean) Oil, *Butyrospermum Parkii* (Shea Butter) | | | 0.5 | | | |
| Polymer JR 400 | Polyquaternium-10 | 0.4 | | | | | |
| Propylene Glycol-1,2 | Propylene Glycol | | | | | | 5 |
| RonaCare Nicotinamide | Niacinamide | | | | | | |
| Sepigel 305 | Polyacrylamide, C 13-14 Isoparaffin, Laureth-7 | | | | | | |
| Silcare Silicone 41M65 | Stearyl Dimethicone | | | | | | |
| Solubilizer | PEG-40 Hydrogenated Castor Oil, Trideceth-9, Propylene Glycol, Water (Aqua) | | | | | 1.5 | 1.3 |
| SymCalmin | Butylene Glycol, Pentylene Glycol, Hydroxyphenyl Propamidobenzoic Acid | 0.1 | | | | | |
| SymClariol | Decylene Glycol | | | | | | |
| SymDiol 68 | 1.2-Hexanediol, Caprylyl Glycol | | 1 | | | 1 | |
| SymGlucan | Water (Aqua), Glycerin, Beta-Glucan | | | 1 | | 5 | |
| SymMatrix | Maltodextrin, *Rubus Fruticosus* (Blackberry) Leaf Extract | | | | | 0.1 | |
| SymMollient W/S | Trideceth-9, PEG-5 Isononanoate, Water (Aqua) | | | | | 2 | |
| SymPeptide 222 | Glycerin, Water (Aqua), Myristoyl Pentapeptide-8 | | | | | | |
| SymRelief | Bisabolol, *Zingiber Officinale* (Ginger) Root Extract | 0.2 | 0.1 | | | | |

| Ingredients | INCI Name | | | | | |
|---|---|---|---|---|---|---|
| SymRepair | Hexyldecanol, Bisabolol, Cetylhydroxyproline Palmitamide, Stearic Acid, *Brassica Campestris* (Rapeseed) Sterols | 1 | 3 | | | |
| SymSitive 1609 | Pentylene Glycol, 4-t-Butylcyclohexanol | | 0.5 | | | |
| SymVital | *Aloe Barbadensis* Leaf Juice Powder, Magnesium Ascorbyl Phosphate, *Rubus Idaeus* (Raspberry) Leaf Extract | | | 0.1 | | |
| SymWhite 377 | Phenylethyl Resorcinol | | | | | |
| Talc | Talc | | | | | |
| Tamasterol | Phytosterols | | | | | |
| Tapioca Pure | Tapioca Starch | | | | | |
| Tego Betaine L7 non preserved | Cocamidopropyl Betain | 8 | | | | |
| Tegosoft PC 31 | Poyglyceryl-3 Caprate | | | | | |
| Triethanolamine, 99% | Triethanolamine | | 0.3 | | | |
| Vitamin A Palmitate | Retinyl Palmitate | 0.05 | | | | |
| Vitamin E Acetate | Tocopheryl Acetate | 0.5 | 0.2 | | | |
| Water | Water (Aqua) | to 100 | to 100 | to 100 | to 100 | to 100 |

| | | Wt. % | | | | |
|---|---|---|---|---|---|---|
| Ingredients | INCI Name | 7 | 8 | 9 | 10 | 11 |
| *Gleditsia triacanthos* Wood Extract, Dried | *Gleditsia triacanthos* Extract | | | | | |
| *Gleditsia triacanthos* Wood Extract (Dry Extract Content 3%) | Propylene Glycol, Water (Aqua), *Gleditsia triacanthos* Extract | 2 | | | | 0.5 |
| *Gleditsia triacanthos* Wood Extract (Dry Extract Content 10%) | Maltodextrin, *Gleditsia triacanthos* Extract | | | 0.5 | 2 | |
| *Gleditsia triacanthos* Wood Extract (Dry Extract Content 1%) | Caprylic/Capric Triglycerides, *Gleditsia triacanthos* Extract | | | | 1 | |
| A-C Polyethylene 9 A | Polyethylene | 5 | | | | |
| Actipone Black Coffee GROW | Water (Aqua), Glycerin, *Coffea Arabica* (Coffee) Seed Extract, *Coffea Robusta* Seed Extract | | 0.5 | | | |
| Actipone *Laminaria Saccharina* | Glycerin, Water (Aqua), *Laminaria Saccharina* Extract | | | | | |
| Actipone Nutgrass (Motha) Root GROW | Water (Aqua), Glycerin, *Cyperus Rotundus* Root Extract | 0.2 | | | | |
| Allantoin | Allantoin | | | | | |
| *Aloe Vera* Gel Conc. 10:1 | *Aloe Barbadensis* Leaf Juice | | | | | 1 |
| Aluminum Stearate | Aluminium Stearate | | | | | |
| Arbutin | B-Arbutin | | | 1.0 | | |
| Arlypon F | Laureth-2 | | | | | |
| Avocado Oil | *Persea Gratissima* (Avocado) Oil | | | | | |
| Biotive L-Arginine | Arginine | | | | | 0.5 |
| Biotive Esculin Sesquihydrate | Esculin | | | 0.1 | | |
| Biotive Troxerutin | Troxerutin | | | | | 0.5 |
| (−)-Alpha-Bisabolol Natural | Bisabolol | | | 0.1 | 0.2 | 0.1 |
| Carbopol Ultrez-10 | Carbomer | | | 0.2 | | |
| Carnitine | Carnitine | | | 0.8 | | |
| Ceramidebio | Cetylhydroxyproline Palmitamide | | | | 0.5 | |
| Citric Acid 10% In Water | Citric Acid | 0.05 | 0.2 | | | |
| Covi-Ox T-70 | Tocopherol | | | | | |
| Crinipan AD | Climbazole | | | | | |
| D-Panthenol | Panthenol | 0.5 | | | | |
| Dermacryl AQF | Acrylates Copolymer | | | | | 2 |
| Dow Corning 200(100 cs) Silicone Fluid | Dimethicone | | | 3 | 0.5 | 0.5 |
| Dow Corning 246 Fluid | Cyclohexasiloxanes, Cyclopentasiloxanes | | | | | 3 |
| Dracorin 100 S.E.P. | Glyceryl Stearate, PEG-100 Stearate | 7 | | | | |

-continued

| | | | | | |
|---|---|---|---|---|---|
| Dracorin CE | Glyceryl Stearate Citrate | | | 1.5 | |
| Dracorin GMS | Glyceryl Stearate | | | 2 | |
| Dracorin GOC | Glyceryl Oleate Citrate, Caprylic/Capric Triglyceride | | | | |
| Dragocalm | Water (Aqua), Glycerin, *Avena Sativa* (Oat) Kernel Extract | | | | |
| Dragocid Liquid | Phenoxyethanol, Methylparaben, Ethylparaben, Butylparaben, Propylparaben, Isobutylparaben | 0.4 | 0.8 | 0.8 | |
| Dragoderm | Glycerin, *Triticum Vulgare* (Wheat) Gluten, Water (Aqua) | | | | |
| Dragosan W/O P | Sorbitan Isostearate, Hydrogenated Castor Oil, Ceresin, Beeswax (Cera Alba) | | | | |
| Dragosantol 100 | Bisabolol | | | | |
| Dragosine | Carnosine | | | | |
| Dragoxat 89 | Ethylhexyl Isononanoate | | | 2 | 2 |
| Edeta B Powder | Tetrasodium EDTA | 0.1 | | | |
| Edeta BD | Disodium EDTA | | 0.1 | | 0.1 |
| Emulgin B2 | Ceteareth-20 | 2 | | | |
| Emulsiphos | Potassium Cetyl Phosphate, Hydrogenated Palm Glycerides | | 1.5 | 2 | 2 |
| Ethanol | Alcohol Denat. | | | | |
| Essential Oil | Essential Oil | | | | |
| Extrapone *Aloe Vera* | Water (Aqua), *Aloe Barbadensis*, Propylene Glycol, Alcohol | | | | |
| Extrapone Butcher's Broom GW P | Glycerin, Water (Aqua), Pentylene Glycol, *Ruscus Aculeatus* Root Extract | 1 | | | |
| Extrapone *Ginkgo Biloba* | Propylene Glycol, Water (Aqua), *Ginkgo Biloba* Leaf Extract, Glucose, Lactic Acid | 0.3 | | | |
| Extrapone Green Tea (Organic) GW | Water (Aqua), Glycerin, *Camellia Sinensis* Leaf Extract | 2 | | | |
| Extrapone Guarana | Water (Aqua), Propylene Glycol, *Paullinia Cupana* Seed Extract, Alcohol | | | | |
| Extrapone Horse Chestnut | Propylene Glycol, Water (Aqua), *Aesculus Hippocastanum* (Horse Chestnut) Seed Extract, Glucose, Lactic Acid | 1 | | | |
| Extrapone Ivy | Propylene Glycol, Water (Aqua), *Hedera Helix* (Ivy) Leaf/Stem Extract, Glucose, Lactic Acid | 0.2 | | | |
| Extrapone Orange Flower | Water (Aqua), Propylene Glycol, *Citrus Aurantium Amara* (Bitter Orange) Flower Extract | 1.0 | | | |
| Extrapone Orange Peel | Water (Aqua), Propylene Glycol, Alcohol, *Citrus Aurantium Dulcis* (Orange) Peel Extract | 1 | | | |
| Extrapone Seaweed | Water (Aqua), Butylene Glycol, *Fucus Vesiculosus* Extract | | 2.5 | | |
| Frescolat MAG | Menthone Glycerin Acetal | | | | |
| Frescolat ML | Menthyl Lactate | | | | |
| Genapol LRO Liquid | Sodium Laureth Sulphate | | | | |
| Givobio GZN | Zinc Gluconate | | | 0.5 | |
| Glycerol | Glycerin | | 3.5 | 3 | 3 |
| Hydrolite 5 | Pentylene Glycol | 5 | | | 2 |
| Hydroviton-24 | Water (Aqua), Pentylene Glycol, Glycerin, Lactic Acid, Sodium Lactate, Serine, Urea, Sorbitol, Sodium Chloride, Allantoin | | | 1 | |

-continued

| | | | | | | |
|---|---|---|---|---|---|---|
| Isoadipate | Diisopropyl Adipate | | | 2 | | |
| Isodragol | Triisononanoin | | | | 3 | 2 |
| Isopropyl palmitate | Isopropyl-Palmitate | 3 | | | | |
| Jojoba Oil | *Simmondsia Chinensis* (Jojoba) Seed Oil | | | | | |
| Jojoba Oil Ethoxylate (Oxypon 328) | Peg-26 Jojoba Acid, Peg-26 Jojoba Alcohol | | 1 | | | |
| Potassium Sorbate | Potassium Sorbate | | | | | |
| Karion F | Sorbitol | 1 | | | | |
| Keltrol CG-RD | Xanthan Gum | | | 0.2 | | 0.4 |
| Koji Acid | Kojic Acid | | | 0.5 | | |
| Caffeine | Caffeine | | 0.5 | | | |
| Lanette 16 | Cetyl Alcohol | 3 | | 1.5 | | 1 |
| Lanette O | Cetearyl Alcohol | | | | 2 | 0.5 |
| Lara Care A-200 | Galactoarabinan | | | | | 0.3 |
| Magnesium Sulphate | Magnesium Sulfate | | | | | |
| Macadamia Nut Oil | *Macadamia Ternifoia* Seed Oil | | | | | |
| Sea Salt (Dead Sea) | Sea Salt (Maris Sal) | 1.5 | | | | |
| Mineral oil | Mineral Oil | | | | | |
| Sodium ascorbyl phosphate | Sodium Ascorbyl Phosphate | | | 1 | | |
| Sodium chloride | Sodium Chloride | | | | | |
| Sodium Hydroxide Soln. 10% in Water | Sodium Hydroxide | | | 0.2 | 0.3 | |
| Neo Actipone White Tea | *Camellia Sinensis* Leaf Extract | 0.1 | | | | |
| Neo Heliopan 303 | Octocrylene | | | | | 10 |
| Neo Heliopan 357 | Butylmethoxydibenzoylmethane | | | 2 | | 3 |
| Neo Heliopan AP, 15% solution, neutralized with L-arginine | Aqua, Disodium Phenyl Dibenzimidazole Tetrasulphonate, Arginine | | | | | 6.7 |
| Neo Heliopan AV | Ethylhexyl Methoxycinnamate | | | 7.5 | | |
| Neo Heliopan BB | Benzophenones-3 | | | 3 | | |
| Neo Heliopan E 1000 | Isoamyl p. Methoxycinnamate | | | | | 1 |
| Neo Heliopan HMS | Homosalate | | | 10 | | 5 |
| Neo Heliopan Hydro, 20% solution, neutralized with Biotive Arginine | Aqua, Phenylbenzimidazole, Sulphonic Acid, Arginine | | | | | 10 |
| Neo Heliopan OS | Ethylhexyl Salicylate | | | 5 | | |
| Neo-PCL Water Soluble N | Trideceth-9, PEG-5 Ethylhexanoate, Water (Aqua) | | | | | |
| Neutral oil | Caprylic/Capric Triglyceride | 10 | | | 10 | |
| Oxynex K Liquid | PEG-8, Tocopherol, Ascorbyl Palmitate, Ascorbic Acid, Citric Acid | 0.1 | | | | |
| Ozokerite Wax 2389 | Ozokerite | | | | | |
| Paraffin oil | Paraffinum Liquidum | | | | | |
| Perfume oil | Parfum (Fragrance) | 0.4 | 0.4 | 0.3 | 0.1 | 0.2 |
| PCL-Liquid 100 | Cetearyl Ethylhexanoate | | | | | |
| PCL-Solid | Stearyl Heptanoate, Stearyl Caprylate | | | | | |
| Pemulen TR-2 | Acrylates/C10-30 Alkyl Acrylate Crosspolymer | | | | | |
| Phytoconcentrole Shea Butter | *Glycine Soja* (Soybean) Oil, *Butyrospermum Parkii* (Shea Butter) | | | | | |
| Polymer JR 400 | Polyquaternium -10 | | | | | |
| Propylene Glycol-1,2 | Propylene Glycol | | | 2 | | |
| RonaCare Nicotinamide | Niacinamide | | | 0.1 | | |
| Sepigel 305 | Polyacrylamide, C 13-14 Isoparaffin, Laureth-7 | | | 2 | | |
| Silcare Silicone 41M65 | Stearyl Dimethicone | | | | | 1 |
| Solubilizer | PEG-40 Hydrogenated Castor Oil, Trideceth-9, Propylene Glycol, Water (Aqua) | | | | | |
| SymCalmin | Butylene Glycol, Pentylene Glycol, Hydroxyphenyl Propamidobenzoic Acid | | | | | |
| SymClariol | Decylene Glycol | | | 0.3 | | |
| SymDiol 68 | 1.2-Hexanediol, Caprylyl Glycol | | | | | |
| SymGlucan | Water (Aqua), Glycerin, Beta-Glucan | | | | | 2 |

-continued

| Ingredients | INCI Name | | | | | |
|---|---|---|---|---|---|---|
| SymMatrix | Maltodextrin, *Rubus Fruticosus* (Blackberry) Leaf Extract | | | | | |
| SymMollient W/S | Trideceth-9, PEG-5 Isononanoate, Water (Aqua) | | | | | |
| SymPeptide 222 | Glycerin, Water (Aqua), Myristoyl Pentapeptide-8 | 5 | | | | |
| SymRelief | Bisabolol, *Zingiber Officinale* (Ginger) Root Extract | | | | 0.1 | |
| SymRepair | Hexyldecanol, Bisabolol, Cetylhydroxyproline Palmitamide, Stearic Acid, *Brassica Campestris* (Rapeseed) Sterols | | | | | |
| SymSitive 1609 | Pentylene Glycol, 4-t-Butylcyclohexanol | | 0.5 | | | |
| SymVital | *Aloe Barbadensis* Leaf Juice Powder, Magnesium Ascorbyl Phosphate, *Rubus Idaeus* (Raspberry) Leaf Extract | 0.5 | | | | |
| SymWhite 377 | Phenylethyl Resorcinol | | 0.5 | | | |
| Talc | Talc | 3 | | | | |
| Tamasterol | Phytosterols | | | 0.3 | | |
| Tapioca Pure | Tapioca Starch | | | | 5 | |
| Tego Betaine L7 non preserved | Cocamidopropyl Betain | | | | | |
| Tegosoft PC 31 | Poyglyceryl-3 Caprate | | | 0.3 | | |
| Triethanolamine, 99% | Triethanolamine | | | | | |
| Vitamin A Palmitate | Retinyl Palmitate | | | | | |
| Vitamin E Acetate | Tocopheryl Acetate | | | 0.3 | 0.5 | |
| Water | Water (Aqua) | to 100 | to 100 | to 100 | to 100 | to 100 |

EXAMPLE 12

Eye Contour Emulsion, SPF15

| Ingredients | INCI Name | Wt. % |
|---|---|---|
| *Gleditsia triacanthos* wood extract (dry extract content 3%) | Propylene Glycol, Water (Aqua), *Gleditsia triacanthos* Extract | 1 |
| Betulin 90% | Betulin | 0.15 |
| Biotive L-Arginine | Arginine | 0.9 |
| Carbopol Ultrez-21 | Acrylates/C10-30 Alkyl Acrylates Crosspolymer | 0.5 |
| Corapan TQ | Diethylhexyl 2,6-Naphthalate | 3 |
| Dracorin GOC | Glyceryl Oleate Citrate, Caprylic/Capric Triglyceride | 1.5 |
| EDTA BD | Disodium EDTA | 0.1 |
| Hydrolite-5 | Pentylene Glycol | 5 |
| Isoadipate | Diisopropyl Adipate | 1 |
| Keltrol CG RD | Xanthan Gum | 0.2 |
| Neo Heliopan 357 | Butylmethoxydibenzoylmethane | 3 |
| Neo Heliopan HMS | Homosalate | 5 |
| Neo Heliopan Hydro, 20% solution, neutralized with arginine | Aqua, Phenylbenzimidazole, Sulphonic Acid, Arginine | 10 |
| Neo Heliopan OS | Ethylhexyl Salicylate | 5 |
| SymFinity 1298 | *Echinacea Purpurea* Extract | 0.1 |
| SymHelios 1031 | Benzylidene Dimethoxydimethylindanone | 0.5 |
| SymMollient L | Neopentyl Glycol Diisononanoate | 2 |
| SymMollient S | Cetearyl Nonanoate | 1 |
| Tegosoft TN | C12-C15 Alkyl Benzoate | 5 |
| Vitamin E Acetate | Tocopheryl Acetate | 0.5 |
| Water | Water (Aqua) | to 100 |

EXAMPLES: 13-15

Oral Preparations

EXAMPLE 13

Fruit Gums

| Ingredients | Wt. % |
|---|---|
| Water | to 100 |
| Sucrose | 34.50 |
| Glucose syrup, DE 40 | 31.89 |
| Iso Syrup C* Tru Sweet 01750 (Cerestar GmbH) | 1.50 |
| Gelatin 240 Bloom | 8.20 |
| Yellow and red food dyes | 0.01 |
| Citric acid | 0.20 |
| *Gleditsia triacanthos* wood extract | 0.075 |

EXAMPLE 14

Gelatin Capsules Suitable for Direct Ingestion

| | Wt. % | | |
|---|---|---|---|
| Ingredients | I | II | III |
| Gelatin shell: | | | |
| Glycerol | 2.014 | 2.014 | 2.014 |
| Gelatin 240 Bloom | 7.91 | 7.91 | 7.91 |

-continued

| Ingredients | Wt. % I | II | III |
|---|---|---|---|
| Aspartame | 0.05 | — | — |
| Sucralose | 0.035 | 0.050 | 0.070 |
| Allura Red (red dye) | 0.006 | 0.006 | 0.006 |
| Brilliant Blue (blue dye) | 0.005 | 0.005 | 0.005 |
| Composition of core: | | | |
| Vegetable oil triglycerides (coconut oil fraction) | to 100 | to 100 | to 100 |
| Flavor G | 9.95 | 12.0 | 12.0 |
| *Gleditsia triacanthos* wood extract | | 0.05 | |
| *Gleditsia triacanthos* wood extract (vegetable oil:dry extract = 90:10) | 3 | | 0.5 |

Flavor G had the following composition (all data in wt. %): 0.1% Neotam Powder, 29.3% peppermint oil arvensis, 29.35% peppermint piperita oil Willamette, 2.97% Sucralose, 2.28% triacetin, 5.4% diethyl tartrate, 12.1% peppermint oil yakima, 0.7% ethanol, 3.36% 2-hydroxyethylmenthyl carbonate, 3.0% 2-hydroxypropylmenthyl carbonate, 5.77% D-limonene, 5.67% L-menthyl acetate.

The gelatin capsules I, II, III suitable for direct ingestion were produced according to WO 2004/050069 and in each case had a diameter of 5 mm, the weight ratio of core material to shell material was 90:10. The capsules all opened in the mouth within less than 10 seconds and dissolved completely within less than 50 seconds.

EXAMPLE 15

Compressed Products in Round Tablet Form

| Ingredients | Wt. % I | II | III |
|---|---|---|---|
| Magnesium stearate | 0.9 | 0.9 | 0.9 |
| Citric acid | 0.2 | 0.2 | 0.2 |
| *Gleditsia triacanthos* wood extract (maltodextrin:dry extract = 95:5) | 1 | | 5 |
| *Gleditsia triacanthos* wood extract | | 0.01 | |
| Dextrose | to 100 | to 100 | to 100 |

EXAMPLES 16-21

Oral Hygiene Products

EXAMPLE 16

Gel Tooth Cream

| Ingredients | I (%) | II (%) | III (%) |
|---|---|---|---|
| Sodium carboxymethylcellulose | 0.40 | 0.40 | 0.40 |
| Sorbitol 70%, in water | 72.00 | 72.00 | 72.00 |
| Polyethylene glycol (PEG) 1500 | 3.00 | 3.00 | 3.00 |
| Saccharin sodium | 0.07 | 0.07 | 0.07 |
| Sodium fluoride | 0.24 | 0.24 | 0.24 |
| p-Hydroxybenzoic acid (PHB) ethyl ester | 0.15 | 0.15 | 0.15 |
| Peppermint flavor | 1.00 | 1.00 | 1.00 |
| *Gleditsia triacanthos* wood extract | 0.10 | 0.02 | 0.001 |
| Abrasive silica | 11.00 | 11.00 | 11.00 |
| Thickening silica | 6.00 | 6.00 | 6.00 |
| Sodium dodecylsulphate | 1.40 | 1.40 | 1.40 |
| Dist. water | to 100 | to 100 | to 100 |

EXAMPLE 17

Tooth Cream Against Plaque

| Ingredients | I (%) | II (%) | III (%) |
|---|---|---|---|
| Carrageenan | 0.90 | 0.90 | 0.90 |
| Glycerol | 15.00 | 15.00 | 15.00 |
| Sorbitol 70%, in water | 25.00 | 25.00 | 25.00 |
| PEG 1000 | 3.00 | 3.00 | 3.00 |
| Sodium fluoride | 0.24 | 0.24 | 0.24 |
| Tetrapotassium diphosphate | 4.50 | 4.50 | 4.50 |
| Tetrasodium diphosphate | 1.50 | 1.50 | 1.50 |
| Saccharin sodium | 0.40 | 0.40 | 0.40 |
| Precipitating silica | 20.00 | 20.00 | 20.00 |
| Titanium dioxide | 1.00 | 1.00 | 1.00 |
| PHB methyl ester | 0.10 | 0.10 | 0.10 |
| Spearmint flavor | 1.10 | 1.10 | 1.10 |
| *Gleditsia triacanthos* wood extract | 0.005 | 0.50 | 0.10 |
| Sodium dodecylsulphate | 1.30 | 1.30 | 1.30 |
| Dist. water | to 100 | to 100 | to 100 |

EXAMPLE 18

Tooth Cream for Sensitive Teeth

| Ingredients | I (%) | II (%) | III (%) |
|---|---|---|---|
| Sodium carboxymethylcellulose | 0.70 | 0.70 | 0.70 |
| Xanthan gum | 0.50 | 0.50 | 0.50 |
| Glycerol | 15.00 | 15.00 | 15.00 |
| Sorbitol 70%, in water | 12.00 | 12.00 | 12.00 |
| Potassium nitrate | 5.00 | 5.00 | 5.00 |
| Sodium monofluorophosphate | 0.80 | 0.80 | 0.80 |
| PHB methyl ester | 0.15 | 0.15 | 0.15 |
| PHB propyl ester | 0.05 | 0.05 | 0.05 |
| Saccharin sodium | 0.20 | 0.20 | 0.20 |
| *Eucalyptus*/menthol flavor | 1.00 | 1.00 | 1.00 |
| *Gleditsia triacanthos* wood extract | 0.03 | 0.30 | 0.006 |
| Calcium carbonate | 35.00 | 35.00 | 35.00 |
| Silicon dioxide | 1.00 | 1.00 | 1.00 |
| Sodium dodecylsulphate | 1.50 | 1.50 | 1.50 |
| Dist. water | to 100 | to 100 | to 100 |

EXAMPLE 19

Mouthwash with Fluoride

| Ingredients | I (%) | II (%) | III (%) |
|---|---|---|---|
| Ethanol | 7.00 | 7.00 | 7.00 |
| Glycerol | 12.00 | 12.00 | 12.00 |
| Sodium fluoride | 0.05 | 0.05 | 0.05 |
| Pluronic F-127 ® (BASF) | 1.40 | 1.40 | 1.40 |

-continued

| Ingredients | I (%) | II (%) | III (%) |
|---|---|---|---|
| Sodium phosphate buffer pH 7.0 | 1.10 | 1.10 | 1.10 |
| Sorbic acid | 0.20 | 0.20 | 0.20 |
| Saccharin sodium | 0.10 | 0.10 | 0.10 |
| Cinnamon/menthol flavor | 0.15 | 0.15 | 0.15 |
| Gleditsia triacanthos wood extract | 0.002 | 0.05 | 0.80 |
| Dye | 0.01 | 0.01 | 0.01 |
| Dist. water | to 100 | to 100 | to 100 |

EXAMPLE 20

Chewing Gum

| Ingredients | I (%) | II (%) | III (%) |
|---|---|---|---|
| Chewing gum base | 21.00 | 21.00 | 21.00 |
| Glucose syrup | 16.50 | 16.50 | 16.50 |
| Glycerol | 0.50 | 0.50 | 0.50 |
| Icing sugar | to 100 | to 100 | to 100 |
| Mint flavor | 1.50 | 1.50 | 1.50 |
| Gleditsia triacanthos wood extract | 0.05 | 0.002 | 0.30 |

EXAMPLE 21

Sugar-Free Chewing Gum

| Ingredients | I (%) | II (%) | III (%) |
|---|---|---|---|
| Chewing gum base | 30.00 | 30.00 | 30.00 |
| Sorbitol, powder | to 100 | to 100 | to 100 |
| Palatinit (isomalt) | 9.50 | 9.50 | 9.50 |
| Xylitol | 2.00 | 2.00 | 2.00 |
| Mannitol | 3.00 | 3.00 | 3.00 |
| Aspartame | 0.10 | 0.10 | 0.10 |
| Acesulfam K | 0.10 | 0.10 | 0.10 |
| Emulgum/emulsifier | 0.30 | 0.30 | 0.30 |
| Sorbitol 70%, in water | 14.00 | 14.00 | 14.00 |
| Glycerol | 1.00 | 1.00 | 1.00 |
| Cinnamon/menthol flavor | 1.50 | 1.50 | 1.50 |
| Gleditsia triacanthos wood extract | 0.003 | 1.0 | 0.20 |

The invention claimed is:

1. A mixture consisting essentially of:
    (a) 0.00001 to 10 wt. % of an extract of the heartwood of Gleditsia triacanthos; and
    (b) one or more polyhydric alcohols selected from the group consisting of 1,2-propanediol, 1,3-propanediol, 1,2-butanediol, 1,3-butanediol, 1,4-butanediol and glycerol.

2. A mixture consisting essentially of:
    (a) 0.00001 to 10 wt. % of an extract of the heartwood of Gleditsia triacanthos; and
    (b) one or more polyhydric alcohols selected from the group consisting of 1,2-propoanediol, 1,3-propanediol, 1,2-butanediol, 1,3-butatendiol, 1,4-butanediol, and glycerol; and
    (c) water.

3. A mixture consisting essentially of:
    (a) 0.00001 to 10 wt. % of an extract of the heartwood of Gleditsia triacanthos; and
    (b) one or more polyhydric alcohols selected from the group consisting of 1,2-propoanediol, 1,3-propanediol, 1,2-butanediol, 1,3-butatendiol, 1,4-butanediol, and glycerol;
    (c) water; and
    (d) one or more preservatives selected from the group consisting of benzoic acid, sodium benzoate, potassium benzoate, propionic acid, sorbic acid, sodium sorbate, potassium sorbate, benzyl alcohol, 1-phenoxypropan-2-ol, and 2-phenoxyethanol.

4. The mixture of claim 3, wherein the one or more preservatives are at least two preservatives selected from the group consisting of benzoic acid, sodium benzoate, potassium benzoate, propionic acid, sorbic acid, sodium sorbate, potassium sorbate, benzyl alcohol, 1-phenoxypropan-2-ol, and 2-phenoxyethanol.

5. The mixture of claim 1, wherein the one or more polyhdric alcohols are in an amount of 20 to 80 wt. %.

6. The mixture of claim 2, wherein the water is in an amount of 10 to 70 wt. %.

7. The mixture of claim 3, wherein the one or more preservatives are in an amount of 0.05 to 5 wt. %.

8. The mixture of claim 3, wherein the one or more polyhdric alcohols are in an amount of 20 to 80 wt. %; the water is in an amount of 10 to 70 wt. %; and the one or more preservatives are in an amount of 0.05 to 5 wt. %.

9. The mixture of claim 8, wherein the one or more polyhdric alcohols are in an amount of 35 to 70 wt. %; the water is in an amount of 10 to 60 wt. %; and the one or more preservatives is in an amount of 0.1 to 2 wt. %.

10. The mixture of claim 1, wherein the heartwood of Gleditsia triacanthos is free of gedistin.

11. The mixture of claim 1, wherein the extract of the heartwood of Gleditsia triacanthos contains fustin.

12. The mixture of claim 1, wherein the heartwood of Gleditsia triacanthos contains fustin and fisetin.

13. The mixture of claim 10, wherein the heartwood of Gleditsia triacanthos contains fustin, fisetin, and protocatechuic acid.

14. The mixture of claim 2, wherein the extract of the heartwood of Gleditsia triacanthos contains fustin.

15. The mixture of claim 14, wherein the heartwood of Gleditsia triacanthos contains fustin and fisetin.

16. The mixture of claim 15, wherein the heartwood of Gleditsia triacanthos contains fustin, fisetin, and protocatechuic acid.

17. The mixture of claim 3, wherein the extract of the heartwood of Gleditsia triacanthos contains fustin.

18. The mixture of claim 17, wherein the heartwood of Gleditsia triacanthos contains fustin and fisetin.

19. The mixture of claim 18, wherein the heartwood of Gleditsia triacanthos contains fustin, fisetin, and protocatechuic acid.

20. A method for treating cellulite in humans consisting essentially of administering or applying a therapeutically effective amount of a mixture according to claim 1 to the human.

* * * * *